(12) United States Patent
Shahaf et al.

(10) Patent No.: US 11,992,604 B2
(45) Date of Patent: May 28, 2024

(54) DEVICES AND METHODS FOR DELIVERING A SUBSTANCE TO A BODY CAVITY

(71) Applicant: SIPNOSE LTD, Yokne'am Ilit (IL)

(72) Inventors: Daniel Shahaf, Kibbutz Dganiya B (IL); Iris Shichor, Zichron Yaakov (IL)

(73) Assignee: SipNose Ltd., Yokne'am Ilit (IL)

( * ) Notice: Subject to any disclaimer, the term of this patent is extended or adjusted under 35 U.S.C. 154(b) by 996 days.

(21) Appl. No.: 16/809,994

(22) Filed: Mar. 5, 2020

(65) Prior Publication Data

US 2020/0197633 A1 Jun. 25, 2020

Related U.S. Application Data

(63) Continuation-in-part of application No. 15/982,996, filed on May 17, 2018, now Pat. No. 11,471,618, (Continued)

(51) Int. Cl.
*A61M 11/00* (2006.01)
*A61M 11/04* (2006.01)
(Continued)

(52) U.S. Cl.
CPC ......... *A61M 11/006* (2014.02); *A61M 11/001* (2014.02); *A61M 11/04* (2013.01);
(Continued)

(58) Field of Classification Search
CPC .. A61M 11/00; A61M 11/001; A61M 11/006; A61M 11/007; A61M 11/008;
(Continued)

(56) References Cited

U.S. PATENT DOCUMENTS

| 462,990 A | 11/1891 | Oppenheimer |
| 3,921,637 A | 11/1975 | Bennie et al. |

(Continued)

FOREIGN PATENT DOCUMENTS

| CN | 1981886 | 6/2007 |
| CN | 104520198 | 4/2015 |

(Continued)

OTHER PUBLICATIONS

PCT International Preliminary Report on Patentability for International Application No. PCT/IL2014/050752, dated Feb. 23, 2016.
(Continued)

*Primary Examiner* — Colin W Stuart
(74) *Attorney, Agent, or Firm* — Foley & Lardner LLP

(57) ABSTRACT

The present invention provides methods and a BFS/FFS device for delivering either one or more substances within at least one body cavity, characterized by a vial comprising $V_{sub}$ [ml] of said substances; said vial from a pierceable container, a blow-fill-seal and a form-fill-seal, having fluid inlet and a fluid discharging outlet of diameter D [mm], configured for placement in proximity to said body cavity; said fluid inlet configured by means of size and shape to interface in a sealable manner a puncturing member, configured to, upon coupling to said fluid inlet, piercing the same, thereby providing said substances in a fluid communication, via a valve, with a chamber configured to accept pressurized fluid at volume $V_{PF}$ [ml] and pressure $P_{PF}$ [barg]; said valve is commutable from an CLOSE to an OPEN CONFIGURATION within a short period of time, <500 milliseconds (dT); at said OPEN CONFIGURATION, said pressurized fluid flows from said chamber, via said fluid inlet, entrains said substances by one erupts via said fluid discharging outlet to within said body cavity.

56 Claims, 22 Drawing Sheets

Related U.S. Application Data which is a continuation-in-part of application No. 14/733,143, filed on Jun. 8, 2015, now Pat. No. 11,116,914.

(60) Provisional application No. 62/117,986, filed on Feb. 19, 2015, provisional application No. 62/077,246, filed on Nov. 9, 2014, provisional application No. 62/526,386, filed on Jun. 29, 2017.

(51) Int. Cl.
*A61M 15/00* (2006.01)
*A61M 15/08* (2006.01)

(52) U.S. Cl.
CPC .......... *A61M 15/002* (2014.02); *A61M 15/08* (2013.01); *A61M 2205/3331* (2013.01); *A61M 2210/0618* (2013.01); *A61M 2210/065* (2013.01); *A61M 2210/0662* (2013.01); *A61M 2210/1089* (2013.01); *A61M 2210/1475* (2013.01)

(58) Field of Classification Search
CPC ...... A61M 11/02; A61M 11/06; A61M 15/00; A61M 15/0001; A61M 15/002; A61M 15/0028; A61M 15/003; A61M 15/0033; A61M 15/0035; A61M 15/0036; A61M 15/0038; A61M 15/004; A61M 15/0041; A61M 15/08; A61M 31/00; A61M 2202/04; A61M 2202/064; A61M 2205/073; A61M 2205/3331; A61M 2210/0618; A61M 2210/0662; A61M 2210/065; A61M 2210/1475

See application file for complete search history.

(56) References Cited

U.S. PATENT DOCUMENTS

| | | |
|---|---|---|
| 4,017,007 A | 4/1977 | Riccio |
| 4,114,615 A | 9/1978 | Wetterlin et al. |
| 4,620,670 A | 11/1986 | Hughes |
| 5,740,794 A | 4/1998 | Smith et al. |
| 6,123,228 A | 9/2000 | Hippensteel |
| 6,186,141 B1* | 2/2001 | Pike ........................ A61B 18/12 128/203.12 |
| 6,398,074 B1 | 6/2002 | Bruna et al. |
| 7,497,390 B2 | 3/2009 | Beller |
| 7,726,308 B1 | 6/2010 | Flora |
| 7,802,569 B2 | 9/2010 | Yeates et al. |
| 7,900,659 B2 | 3/2011 | Whitley et al. |
| 8,360,056 B2* | 1/2013 | Ishizeki ............ A61M 15/0035 128/203.15 |
| 2001/0008637 A1* | 7/2001 | Hochrainer ....... A61M 15/0028 424/451 |
| 2002/0023641 A1 | 2/2002 | Stadelhofer |
| 2002/0092520 A1 | 7/2002 | Casper |
| 2002/0092524 A1 | 7/2002 | Lockhart et al. |
| 2003/0079743 A1 | 5/2003 | Genova et al. |
| 2003/0127533 A1 | 7/2003 | Stihl |
| 2003/0187404 A1 | 10/2003 | Waldenburg |
| 2003/0209455 A1 | 11/2003 | Pynson et al. |
| 2005/0028812 A1 | 2/2005 | Djupesland |
| 2006/0067911 A1 | 3/2006 | Nilsson |
| 2006/0107957 A1 | 5/2006 | Djupesland |
| 2006/0151629 A1 | 7/2006 | Vedrine et al. |
| 2006/0213514 A1 | 9/2006 | Price et al. |
| 2006/0254583 A1* | 11/2006 | Deboeck ............... A61K 9/0075 128/203.15 |
| 2006/0254585 A1* | 11/2006 | Ishizeki ............ A61M 15/0043 128/203.15 |
| 2007/0060868 A1 | 3/2007 | Tsutsui |
| 2007/0125371 A1 | 6/2007 | Djupesland |
| 2007/0151562 A1 | 7/2007 | Jones et al. |
| 2007/0154407 A1 | 7/2007 | Peters et al. |
| 2007/0256688 A1* | 11/2007 | Schuster ........... A61M 15/0028 424/45 |
| 2008/0092887 A1 | 4/2008 | Hodson et al. |
| 2008/0210229 A1 | 9/2008 | Corbacho |
| 2009/0285849 A1 | 11/2009 | Barsanti et al. |
| 2009/0314293 A1 | 12/2009 | Djupesland |
| 2010/0083963 A1* | 4/2010 | Wharton ............. A61M 15/009 128/203.15 |
| 2010/0282246 A1 | 11/2010 | Djupesland |
| 2011/0048414 A1 | 3/2011 | Hoekman |
| 2011/0088690 A1 | 4/2011 | Djupesland et al. |
| 2011/0168172 A1 | 7/2011 | Patton |
| 2011/0283996 A1 | 11/2011 | Abrams |
| 2012/0291779 A1 | 11/2012 | Haartsen et al. |
| 2013/0096495 A1 | 4/2013 | Holmqvist et al. |
| 2013/0180524 A1 | 7/2013 | Shahaf |
| 2013/0267864 A1 | 10/2013 | Addington et al. |
| 2013/0299607 A1 | 11/2013 | Wilkerson et al. |
| 2013/0345673 A1 | 12/2013 | Ferreri et al. |
| 2014/0060532 A1 | 3/2014 | Hodges et al. |
| 2015/0122257 A1 | 5/2015 | Winkler et al. |
| 2015/0144129 A1 | 5/2015 | Djupesland |
| 2015/0174343 A1 | 6/2015 | Muellinger et al. |
| 2015/0209325 A1 | 7/2015 | Najarian et al. |
| 2015/0297845 A1 | 10/2015 | Shahaf et al. |
| 2016/0129205 A1 | 5/2016 | Shahaf et al. |
| 2018/0072480 A1 | 3/2018 | Genosar |
| 2018/0110922 A1 | 4/2018 | Dunki-Jacobs et al. |
| 2019/0015613 A1 | 1/2019 | Shahaf et al. |
| 2019/0060168 A1 | 2/2019 | Koska |
| 2020/0197631 A1 | 6/2020 | Stedman et al. |
| 2020/0197633 A1 | 6/2020 | Shahaf et al. |
| 2020/0289768 A1 | 9/2020 | Shahaf et al. |
| 2020/0289769 A1* | 9/2020 | Poullain ............ A61M 15/0041 |
| 2020/0306463 A1 | 10/2020 | Shahaf et al. |

FOREIGN PATENT DOCUMENTS

| | | |
|---|---|---|
| CN | 107580513 | 1/2018 |
| DE | 19502725 | 8/1996 |
| DE | 9708406 | 9/1998 |
| DE | 202013105715 U1 | 2/2014 |
| EP | 1 023 098 B1 | 9/2004 |
| EP | 1 752 176 A1 | 2/2007 |
| EP | 2030645 A1 | 3/2009 |
| EP | 2 922 770 | 9/2015 |
| GB | 724974 | 2/1953 |
| GB | 2415376 A | 12/2005 |
| JP | 2002-505981 A | 2/2002 |
| WO | 90/12567 A1 | 11/1990 |
| WO | WO-99/58180 | 11/1999 |
| WO | WO-2009/002267 | 12/2008 |
| WO | 2012/029064 A1 | 3/2012 |
| WO | 2013/0128447 A1 | 9/2013 |
| WO | WO-2015/025324 A1 | 2/2015 |
| WO | WO-2016/054742 | 4/2016 |
| WO | WO-2016/199135 A1 | 12/2016 |
| WO | WO-2018/051371 | 3/2018 |
| WO | WO-2019/003216 A1 | 1/2019 |
| WO | WO-2019/073165 | 4/2019 |
| WO | WO-2019/079335 | 4/2019 |
| WO | WO-2019/220443 A1 | 11/2019 |
| WO | WO-2020/154182 | 7/2020 |

OTHER PUBLICATIONS

PCT International Search Report for International Application No. PCT/IL2014/050752, dated Dec. 18, 2014.

PCT International Written Opinion for International Application No. PCT/IL2014/050752, dated Dec. 18, 2014.

Damm et al., "Intranasal Volume and Olfactory Function", Chemical Senses, 2002, pp. 831-839, vol. 27, Oxford University Press.

Derendorf et al., "Molecular and clinical pharmacology of intranasal corticosteroids: clinical and therapeutic implications", Allergy, 2008, pp. 1292-1300, vol. 63, 2008 Blackwell Munksgaard.

(56) References Cited

OTHER PUBLICATIONS

Doose et al., "Single-dose pharmacokinetics and effect of food on the bioavailability of topiramate, A novel antiepileptic drug", Journal of Clinical Pharmacology, 1996, pp. 884-891, vol. 36.

Ganger et al., "Tailoring Formulations for Intranasal Nose-to-Brain Delivery: A Review on Architecture, Physico-Chemical Characteristics and Mucociliary Clearance of the Nasal Olfactory Mucosa", Pharmaceutics, 2018, pp. 1-28, vol. 10, No. 116.

Khan et al., "Progress in brain targeting drug delivery system by nasal route", Journal of Controlled Release, 2017, pp. 364-389, vol. 268, Elsevier B.V.

Lammi et al., "Treatment with intranasal iloprost reduces disease manifestations in a murine model of previously established COPD", The American Journal of Physiology—Lung Cellular and Molecular Physiology, 2016, pp. L630-L638, vol. 310, 2016 American Physiological Society.

Leombruni et al., "Treatment of obese patients with binge eating disorder using topiramate: a review", Neuropsychiatric Disease and Treatment, 2009, pp. 385-392, vol. 5, Dove Medical Press Ltd.

Massolt et al., "Appetite suppression through smelling of dark chocolate correlates with changes in ghrelin in young women", Regulatory Peptides, 2010, pp. 81-86, vol. 161, 2010 Elsevier B.V.

Puhakka et al., "The common cold: Effects of intranasal fluticasone propionate treatment", The Journal of Allergy and Clinical Immunology, 1998, pp. 726-731, vol. 101, No. 6, Part 1, Mosby, Inc.

Ramaekers et al., "Odors: appetizing or satiating? Development of appetite during odor exposure over time", International Journal of Obesity, 2014, pp. 650-656, vol. 38, 2014 Macmillan Publishers Limited.

Scheibe et al., "Intranasal Administration of Drugs", Archives of Otolaryngology—Head & Neck Surgery, Jun. 2008, pp. 643-646, vol. 134, No. 6, 2008 American Medical Association.

Schiffman et al., "Taste and smell perception affect appetite and immunity in the elderly", European Journal of Clinical Nutrition, 2000, pp. S54-S63, Suppl 3, 2000 Macmillan Publishers Ltd.

Schriever et al., "Size of nostril opening as a measure of intranasal volume", Physiology & Behavior, 2013, pp. 3-5, vol. 110-111, 2012 Elsevier Inc.

Yeomans, "Olfactory influences on appetite and satiety in humans", Physiology and Behavior, 2006, pp. 1-14, vol. 89, No. 1.

Foreign Search Report on EP 21891341.6 DTD Feb. 12, 2024.

Supplemental European Search Report in EP 21 76 4082 DTD Feb. 2, 2024.

\* cited by examiner

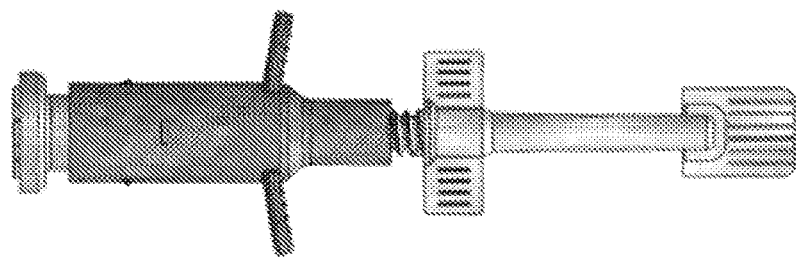
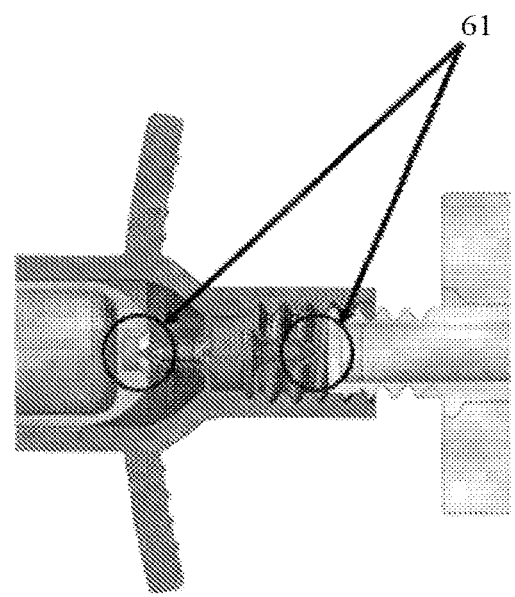
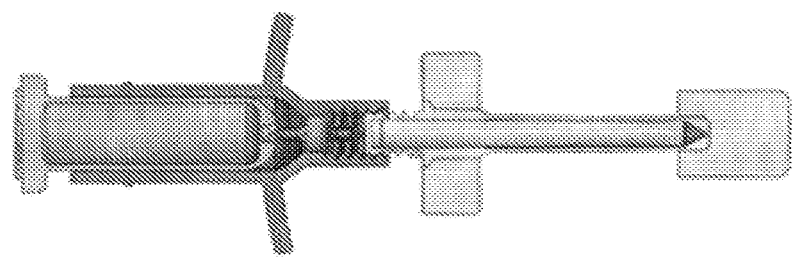
Fig. 6A

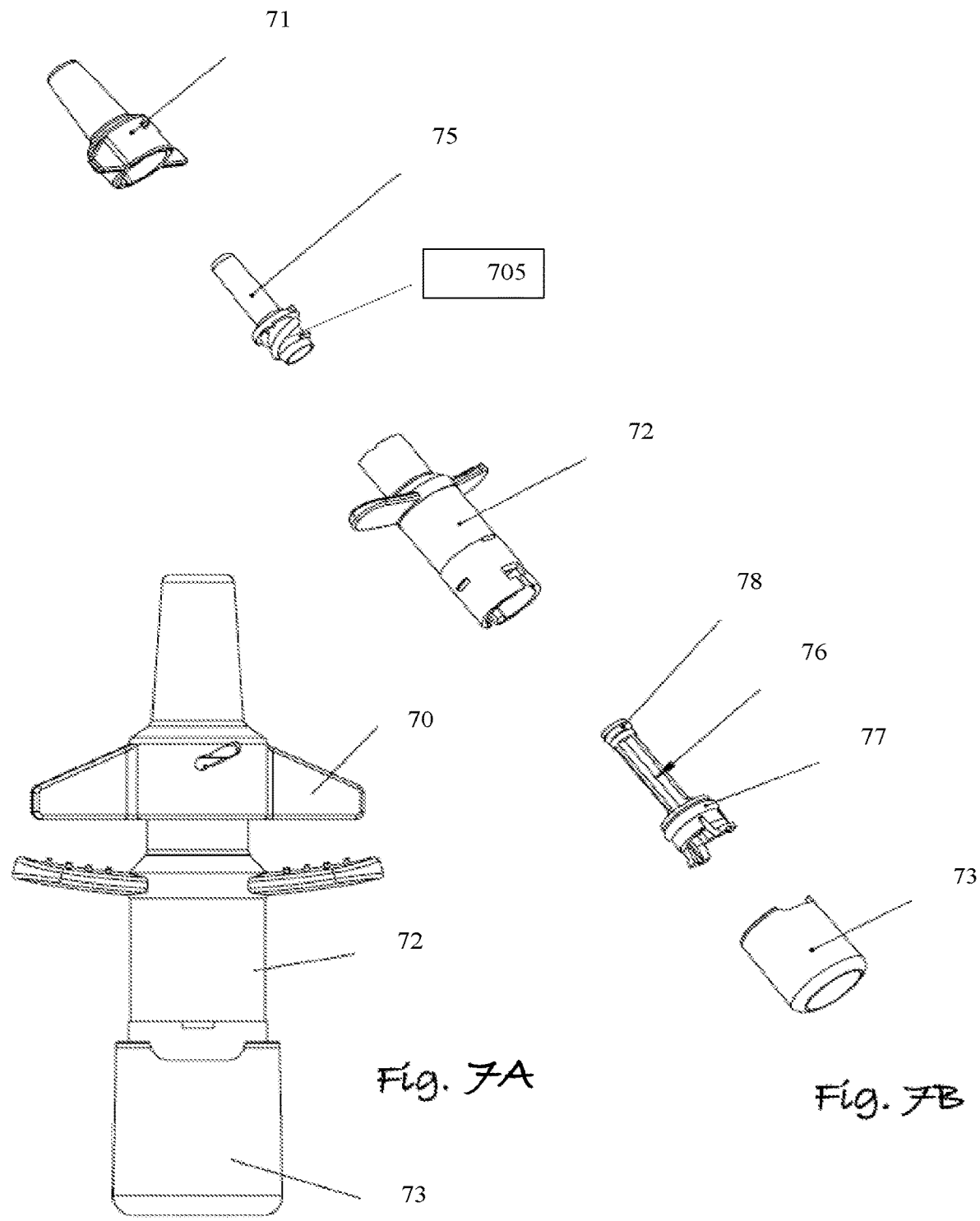

DEVICES AND METHODS FOR DELIVERING A SUBSTANCE TO A BODY CAVITY

CROSS REFERENCE TO RELATED APPLICATIONS

This Application is a Continuation-in-Part of U.S. application Ser. No. 15/982,996, filed on May 17, 2018 which is a Continuation-in-Part of U.S. Non-Provisional application Ser. No. 14/733,143 filed on Jun. 8, 2015 which claims priority to and the benefit of U.S. Provisional Application Nos. 62/117,986 filed on Feb. 19, 2015 and 62/077,246 filed on Nov. 9, 2014. U.S. application Ser. No. 15/982,996 also claims priority to and the benefit of U.S. Provisional Application No. 62/526,386 filed on Jun. 29, 2017.

This Application is a Continuation-in Part of U.S. application Ser. No. 16/810,096 filed Mar. 5, 2020, which is a Continuation-In-Part of U.S. application Ser. No. 15/982,630, filed on May 17, 2018 which is a Continuation-in-Part of U.S. Non-Provisional application Ser. No. 14/733,143 filed on Jun. 8, 2015 which claims priority to and the benefit of U.S. Provisional Application Nos. 62/117,986 filed on Feb. 19, 2015 and 62/077,246 filed on Nov. 9, 2014. U.S. application Ser. No. 15/982,630 also claims priority to and the benefit of U.S. Provisional Application No. 62/507,816 filed on May 18, 2017.

Further, this application is a Continuation-in-Part of U.S. application Ser. No. 14/433,048 filed on Apr. 2, 2015, which is National Phase Entry of PCT/IL2014/050752 filed on Aug. 21, 2014, which claims the benefit of and priority to U.S. Provisional Application No. 61/868,614 filed on Aug. 22, 2013, U.S. Provisional Application No. 61/868,627 filed on Aug. 22, 2013, and German Application No. 2020131057150 filed on Dec. 16, 2013.

The contents of the above applications are all incorporated by reference as if fully set forth herein in their entirety.

FIELD OF THE INVENTION

The present invention generally pertains to a system and methods for delivering aerosolized substance to a natural orifice of the body.

BACKGROUND OF THE INVENTION

Blow-Fill-Seal (BFS) technology is a manufacturing technique used to produce small (0.1 ml) and large (<500 ml) liquid-filled containers. The basic concept of blow-fill-seal and form-fill-seal (referred to interchangeably hereinafter as BFS) is that a container is formed, filled and sealed in a continuous process without human intervention in a sterile or aseptic enclosed area. Thus, this technology can be used to sterile or aseptically packaging and manufacturing of pharmaceutical liquid dosage forms.

There are several ways of manufacturing. According to one method, the processes begun as pharmaceutical grade plastic resin is vertically heat-extruded through a circular throat to form a hanging tube (parison). This extruded tube is then enclosed within a two-part mold and the tube is cut above the mold. The mold is zone, or a sterile filling space, where filling needles (mandrels) are lowered and used to inflate the plastic to form a container within the mold. Following formation of the container, the mandrel is used to fill the container with the liquid. Following filling, the mandrels are retracted and a secondary top mold seals the container. All actions take place within the sterile enclosed area, a sterile shrouded chamber within the machine. The product can then be discharged to a non-sterile area for labeling, packaging and distribution.

BFS technology reduces personnel intervention, making it a more robust method for aseptic preparation of sterile pharmaceuticals. BFS is used for the filling of vials for parenteral preparations and infusion, eye drops, and inhalation products. Generally, the containers are made of polyethylene and polypropylene.

It is therefore a long felt need to provide a system which provides an efficient delivery of a substance to a target site from such BFS containers, provides sufficient material to the target site, and ensures reproducibility.

SUMMARY OF THE INVENTION

This application incorporates herein by reference the contents of U.S. application Ser. No. 15/982,996 in its entirety.

It is an object of the present invention to disclose a device for delivering either one or more substances within at least one body cavity. The device is characterized by at least one pierceable vial comprising $V_{sub}$ [ml or mg] of the substances; the vial having at least one fluid inlet port of diameter $D_{in}$ [mm] and at least one fluid discharging outlet port of diameter $D_{out}$ [mm], configured for placement in proximity to the body cavity; the fluid inlet port configured by means of size and shape to interface with at least one puncturing member, configured to, upon coupling to the fluid inlet port, piercing the same, thereby providing the substances in a fluid communication, with at least one chamber configured to accept pressurized fluid at volume $V_{PF}$ [ml] and pressure $P_{PF}$ [barg]; the pressurized fluid flows from the chamber, via the fluid inlet port, entrains the substances, erupts via the fluid discharging outlet port to within the body cavity in the form of aerosol, such that the release time of the $V_{sub}$ [ml or mg] of the substances and the $V_{PF}$ [ml] of the pressurized fluid, $dT_{release}$ is less than 500 milliseconds; In this device, the following held: $V_{PF}$ is in a range of 1 to 50 ml; $V_{sub}$ is in a range of about 0.01 to about 7 ml or 0.1 mg to 7 g; $P_{PF}$ is in a range of about 0 to about 10 barg; further wherein at least one of the following is being held true: $D_{in}$ or $D_{out}$ are in a range of 0.2 to 6 mm; the pressure velocity is greater than 0.001 barg/ms; the pressure velocity is greater than 0.01 barg/ms; the volume rate $dV_{sub}/dT_{release}$ is greater than 0.0001 ml/ms; the volume rate $dV_{sub}/dT_{release}$ is greater than 0.001 ml/ms; the volume rate $dV_{PF}/dT_{release}$ is greater than 0.001 ml/ms; the volume rate $dV_{PF}/dT_{release}$ is greater than 0.01 ml/ms; any combination thereof. The vial is further selected from a group consisting of a pierceable container, a blow-fill-seal and a form-fill-seal and any combination thereof.

It is another of the present invention to disclose the device as disclosed above, wherein the vial comprises a cap adapted to seal the vial, such that removal thereof provides fluid communication between the vial and the body cavity through the fluid discharging outlet port.

It is another of the present invention to disclose the device as disclosed in any of the above, wherein the at least one puncturing member is adapted to pierce the vial be means of a screw mechanism, such that rotation of the nosepiece cover along the screw mechanism in the base enables the pierce of the fluid inlet port in the vial by means of the puncturing member.

It is another of the present invention to disclose the device as defined in any of the above, wherein at least one of the following is true: (a) The body cavity is selected from a group consisting of nasal cavity, the mouth, the throat, an ear, the vagina, the rectum, the urethra, and any combination thereof. (b) The pressurized gas is selected from a group consisting of air, nitrogen, oxygen, carbon dioxide, helium, neon, xenon and any combination thereof. (c) During dispensing of the at least one substance, a mixture of the predetermined volume $V_{gas}$ [ml] of the pressurized gas with the predetermined volume $V_{sub}$ [ml or mg] of the substance entrained within it forms a plume of aerosol; the aerosol having a predetermined distribution, the distribution being either homogeneous or heterogeneous, the heterogeneous distribution is selected from a group consisting of: an arbitrary distribution, a distribution in which the density of the at least one substance within the mixture follows a predetermined pattern, and any combination thereof; characteristics of the aerosol selected from a group consisting of: particle size, particle shape, particle distribution, and any combination thereof, are determinable from characteristics of the device selected from a group consisting of: the predetermined volume of the pressurized gas, the predetermined volume of the substance, the predetermined pressure of the pressurized gas, the predetermined orifice size, and any combination thereof. (d) At least one the substance is selected from a group consisting of a gas, a liquid, a powder, an aerosol, a slurry, a gel, a suspension and any combination thereof. (e) The least one the substance is stored under either an inert atmosphere or under vacuum to prevent reactions during storage. (f) A dose-response curve is substantially linear for brain concentration of the substance when administered nasally via the device; and (g) A dose-response curve for brain concentration having a fit selected from a group consisting of logarithmic, parabolic, exponential, sigmoid, power-low, and any combination thereof; of the substance when administered nasally via the device.

It is another of the present invention to disclose the device as disclosed in any of the above, wherein the vial is a capsule having a main longitudinal axis, the capsule comprising a number n of compartments, the capsule configured to contain the predetermined volume $V_{sub}$ [ml or mg] of the at least one substance, the volume $V_{sub}$ [ml or mg] of the at least one substance containable in at least one of the n compartments; at least one of the following being true: the number n of the compartments is an integer greater than or equal to 1; at least one the compartment has cross-section with shape selected from a group consisting of: wedge shaped, circular, oval, elliptical, polygonal, annular, and any combination thereof; for the number n of compartments being an integer greater than 1, at least two the compartments have different volumes; for the number n of compartments being an integer greater than 1, at least two the compartments have the same volume; for the number n of compartments being an integer greater than 1, at least two the compartments have different cross-sectional areas; for the number n of compartments being an integer greater than 1, at least two the compartments have the same cross-sectional area; for the number n of compartments being an integer greater than 1, at least two the compartments contain different substances; for the number n of compartments being an integer greater than 1, at least two the compartments contain the same substance; for the number n of compartments being an integer greater than 1, at least two the compartments are disposed coaxially around the main longitudinal axis of the capsule; for the number n of compartments being an integer greater than 1, at least two the compartments are disposed sequentially along the main longitudinal axis of the capsule; for the number n of compartments greater than 1, the plurality of substances mix during the dispensing; and for the number n of compartments greater than 1, the plurality of substances react during the dispensing.

It is another of the present invention to disclose the device as disclosed in any of the above, wherein the vial comprises a port fluidly connectable to the exterior of the device, the port configured such that the at least one substance is insertable into the chamber via the port.

It is another object of the present invention to disclose the device as disclosed above, wherein the device comprises a port cover configured to provide an air-tight closure for the port, the port cover slidable along the device, rotatable around the device, rotatable around a hinge on the exterior of the device and any combination thereof.

It is another of the present invention to disclose the device as disclosed in any of the above, wherein the pressurized fluid entrains the substance in a pulsed manner, such that a plurality of portions $V_{PF}$ erupts via the fluid discharging outlet to within the body cavity It is another object of the present invention to disclose a method for delivering either one or more substances within at least one body cavity, characterized by steps of providing at least one pierceable vial with $V_{sub}$ [ml or mg] of the substances; the vial having at least one fluid inlet port of diameter $D_{in}$ [mm] and at least one fluid discharging outlet port of diameter $D_{out}$ [mm], configured for placement in proximity to the body cavity; configuring the fluid inlet by means of size and shape to interface a puncturing member, so that upon coupling to the fluid inlet port, piercing of the same, thereby providing the substances in a fluid communication, with at least one chamber configured to accept pressurized fluid at volume $V_{PF}$ [ml] and pressure $P_{PF}$ [barg]; and facilitating the flow of the pressurized fluid from the chamber, via the fluid inlet, entrains the substances, erupts via the fluid discharging outlet port into the body cavity, such that the release time of the $V_{sub}$ [ml or mg] of the substances and the $V_{PF}$ [ml] of the pressurized fluid, $dT_{release}$ is less than 500 milliseconds. The method further held the followings: $V_{PF}$ is in a range of 1 to 50 ml; $V_{sub}$ is in a range of about 0.01 to about 7 ml or 0.1 mg to 1 g; $P_{PF}$ is in a range of about 0 to about 10 barg/The following is further being held true: $D_{in}$ or $D_{out}$ are in a range of 0.2 to 6 mm; the pressure velocity is greater than 0.001 barg/ms; the pressure velocity is greater than 0.01 barg/ms; the volume rate or $dV_{sub}/dT_{release}$ is greater than 0.0001 ml/ms; the volume rate $dV_{sub}/dT_{release}$ is greater than 0.001 ml/ms; the volume rate $dV_{PF}/dT_{release}$ is greater than 0.001 ml/ms; the volume rate $dV_{PF}/dT_{release}$ is greater than 0.01 ml/ms; and any combination thereof. Additionally, the step of providing the vial additionally comprising step of selecting the vial from a group consisting of a pierceable container, a blow-fill-seal and a form-fill-seal and any combination thereof.

It is another of the present invention to disclose the method as disclosed above, wherein it additionally comprising at least one of the following steps: selecting the body cavity from a group consisting of a nasal cavity, the mouth, the throat, an ear, the vagina, the rectum, the urethra, and any combination thereof; selecting the gas from a group consisting of: air, nitrogen, oxygen, carbon dioxide, helium, neon, xenon and any combination thereof; dispensing the at least one substance, and during the step of dispensing, forming a plume of aerosol with predetermined distribution from a mixture of the predetermined volume $V_{gas}$ [ml] of the pressurized gas and the predetermined volume $V_{sub}$ [ml]

entrained within it; selecting the predetermined distribution from a group consisting of: a homogeneous distribution, a heterogeneous distribution; selecting the heterogeneous distribution from a group consisting of: an arbitrary distribution, a distribution in which the density of the at least one substance within the mixture follows a predetermined pattern, and any combination thereof; selecting characteristics of the aerosol from a group consisting of: particle size, particle shape, particle distribution, and any combination thereof, are determinable from characteristics of the device selected from a group consisting of: the predetermined volume of the pressurized gas, the predetermined volume of the substance, the predetermined pressure of the pressurized gas, the predetermined orifice size, and any combination thereof;

selecting the substance from a group consisting of: a gas, a liquid, a powder, a slurry, a gel, a suspension, and any combination thereof; storing at least one the substance under either an inert atmosphere or under vacuum, thereby preventing reactions during storage; and characterizing a dose-response curve for brain concentration of the substance to be of substantially linear form; and a dose-response curve for brain concentration having a fit selected from a group consisting of logarithmic, parabolic, exponential, sigmoid, power-low, and any combination thereof; of the substance when administered nasally via the device.

BRIEF DESCRIPTION OF THE DRAWINGS

The invention is herein described, by way of example only, with reference to the accompanying drawings, wherein:

FIG. 5G showing the device after activation;

FIGS. 6A-E show another embodiment of the present invention, with FIG. 6A illustrating a front view of a pre-used device carrying a BFS and cross sections of the same; FIG. 6B showing securing of the BFS to the device and breaking the cap; FIG. 6C presenting a cross-section view; FIG. 6D showing a button at the base of the device being pushed; FIG. 6E showing pressurized fluid flowing from the container to the BFS and carrying the drug outward;

FIGS. 7A-7B illustrating a device being another embodiment of the present invention, a front and exploded view, respectively;

DETAILED DESCRIPTION OF THE PREFERRED EMBODIMENTS

Figure 1A:
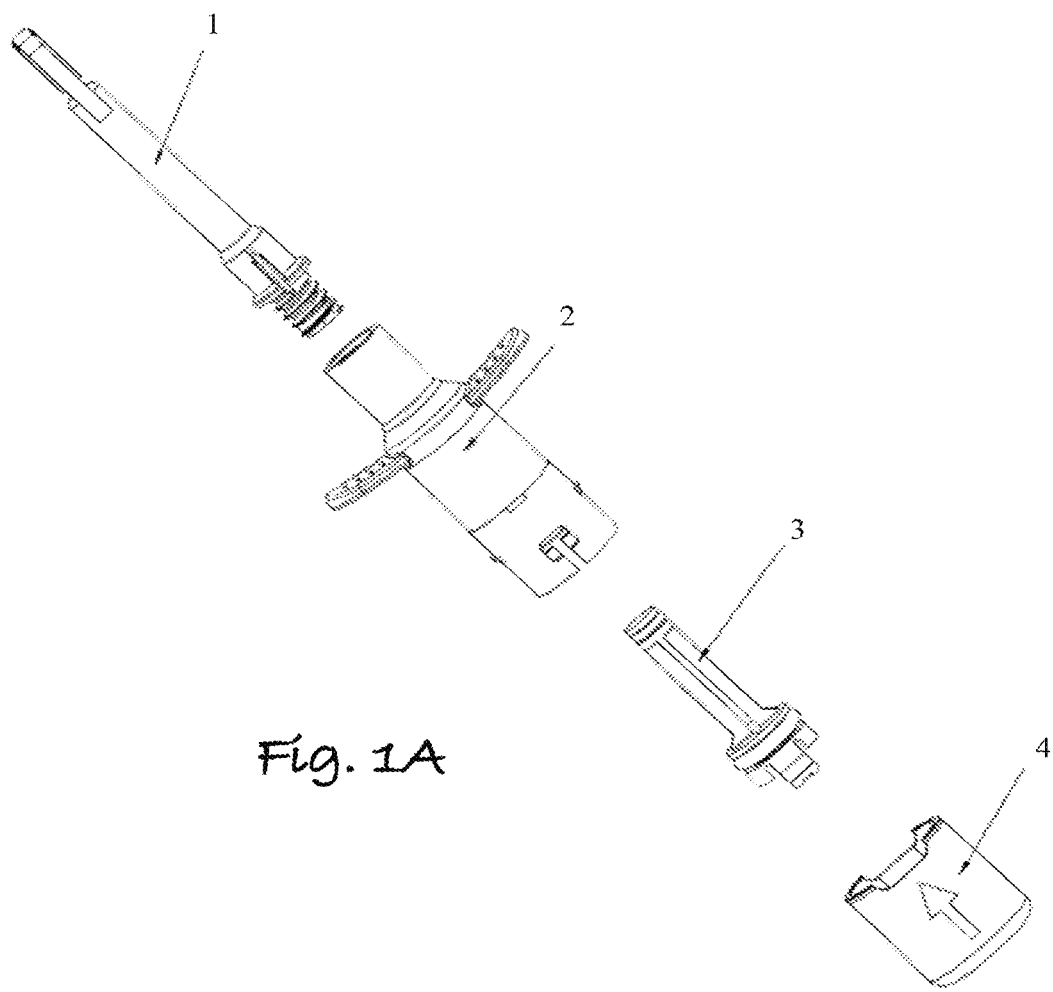
FIGS. 1A-B shows an embodiment of the present invention, with FIG. 1A showing an exploded view of the device and FIG. 1B showing the device fully assembled.

This application incorporates herein by reference the contents of U.S. application Ser. No. 15/982,996 in its entirety.

The following description is provided, alongside all chapters of the present invention, so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide a device capable of improving the transfer of medicament to a predetermined desired location and to provide a device capable of improving the delivery of medicament through the tissue.

In the present invention, a combination of parameters and forces such as pressure, gas/air volume orifice diameter enable the formation of optimized aerosol characteristics for both improved delivery of aerosol to the target area (such as the olfactory epithelium in the nasal cavity) and enhanced absorption at that area for better delivery to a desired tissue (such as the brain).

The term 'ul' or 'µm' hereinafter refers to the unit micro liters or micro meters, respectively.

The term 'capsule' interchangeably 'container' interchangeably refer to a container configured to contain a flowable substance. The term flowable refers hereinafter to any liquid, gas, aerosol, powder and any combination thereof. It should be emphasized that the term capsule can also refer to a predefined volume within the same in which a flowable substance is placed. In other words, the predefined volume is sized and shaped to enclose a predefined volume of the substance.

The term 'plurality' hereinafter refers to an integer greater than or equal to one.

The term 'olfactory epithelium' hereinafter refers to a specialized epithelial tissue inside the nasal cavity. The olfactory epithelium lies in the upper top portion of the nasal cavity.

The term 'substance' hereinafter refers to any substance capable of flowing. Such a substance can be a granular material, including a powder; a liquid; a gel; a slurry; a suspension; and any combination thereof. The term further refers to one or more members of a group consisting of proteins; stem-cells; cells, organs, portions, extracts, and isolations thereof, macro-molecules; RNA or other genes and proteins-encoding materials; neurotransmitters; receptor antagonists; biologic response modifiers; hormones; Ketamine; commercially available by Lilly (US) Baqsimi product; Glucagon, biologic response modifiers; Glucagon; substrates to treat one of eth followings: anaphylaxis, Parkinson, seizures and opioid overdose; epinephrine; atropine; metoclopramide; commercially available Naloxone or Narcan products; Esketamine (Spravato); Radicava [edaravone]; Ingrezza [valbenazine]; Austedo [deutetrabenazine]; Ocrevus [ocrelizumab]; Xadago [safinamide]; Spinraza

[nusinersen]; Zinbryta [daclizumab]; Nuplazid [pimavanserin]; Aristada [aripiprazole lauroxil]; Vraylar [cariprazine]; Rexulti [brexpiprazole]; Aptiom [eslicarbazepine acetate]; Vizamyl [flutemetamol F18 injection]; Brintellix [vortioxetine]; Tecfidera [dimethyl fumarate]; Dotarem [gadoterate meglumine]; Antibody mediated brain targeting drug delivery including aducanumab, gantenerumab, bapineuzumab, solanezumab, ofatumumab CD20, BIIB033, LCN2, HMGB1; insulin; oxytocin; orexin-A; leptin; benzodiazepine i.e. midazolam; naloxone; perillyl alcohol; camptothecin; phytochemicals including curcumin and chrysin; nucleotides; olanzapine; risperidone; Venlafaxin; GDF-5; zonisamide; ropinirole; plant-originated and synthetically-produced terpenes and cannabinoids, including THC and CBD; valproric acid; rivastigmine; estradiol; topiramate or an equivalent preparation comprising CAS No. 97240-79-4; MFSD2 or MFSD2A or sodium-dependent lysophosphatidylcholine symporter; and any esters, salts, derivatives, mixtures, combinations thereof, with or without a carrier, liposomes, lyophilic or water-miscible solvents, surfactants, cells, cells fractions, at a therapeutically effective concentration.

The term 'gas' refers to any fluid that can be readily compressed. Gases as used herein include, but are not limited to, air, nitrogen, oxygen, carbon dioxide, helium, neon, xenon and any combination thereof. Devices charged by hand will typically use air as the carrier gas.

The term 'fluid' refers to any substance or mixtures of substances that continually deforms (flows) under an applied shear stress, or external force. This term refers to gas, liquids, particulate or granulated solids (powders), aerosols, and any mixtures and combinations thereof.

The term 'about' refers hereinafter to a range of 25% below or above the referred value.

The term "body orifice" and "body cavity" are interchangeably refer to one or more of the followings: nasal cavity, a mouth, a throat, an ear, a vagina, a rectum, a urethra, and any combination thereof.

The term 'biologic' or 'biologic response modifier' hereinafter refers to material manufactured in or extracted from biological sources such as a genetically engineered protein derived from human genes, or a biologically effective combination of such proteins.

All pressures herein are gauge pressures, relative to atmospheric pressure. Pressure units will be written herein using the standard abbreviation for "gauge', namely, "g". For example, atmospheric pressure is 0 barg and a pressure of 1 bar above atmospheric is 1 barg.

The term 'release time' refers hereinafter to the time for the drug and carrier gas to substantially completely exit the device. Typically, the release time is affected by the combination of the Volume of substance, volume of pressurized gas, pressure of pressurized gas, the orifice diameter, the activation time of the valve that reflects the time for the device to reconfigure from the ACTIVE configuration to the INACTIVE configuration or vice versa and any combination thereof.

The terms 'the device', 'the present device', 'the SipNose device' and 'SipNose' will be used interchangeably to refer to a device according to any embodiment of the present invention.

In all of the embodiments of the device shown hereinbelow, identical numbers refer to identical functions. All figures shown herein are illustrative and none is to scale.

The present invention teaches a device for delivering a predetermined amount of a substance, preferably comprising a medication or combination of medications, into a body orifice of a subject, the orifice comprising any of the body's natural orifices, including a nostril, the mouth, the ear, the throat, the urethra, the vagina, the rectum and any combination thereof.

In preferred embodiments of the device, the device comprises a delivery mechanism and a medicament capsule, as described hereinbelow. The device can apply a broad range of drugs and materials to the nasal cavity for local effect, deliver a broad range of drugs and materials through the nasal cavity to the systemic circulation, deliver a broad range of drugs and materials through the nasal cavity to the central nerve system (CNS) the brain, spinal cord and associated nerves, and any combination thereof.

The drugs to be applied could be, but are not limited to, pharmaceuticals, natural compounds, biologics, hormones, peptides, proteins, viruses, cells, stem cells and any combination thereof.

However, it should be emphasized that the device can be provided alone as well as in combination with a capsule.

In some cases, the capsule would be provided with a known medicament within the same and in other cases the capsule would be 'filled' with the medicament just before use.

In some embodiments of the present invention, the device operating characteristics and the substance characteristics can be jointly optimized to maximize uptake of the substance at the desired site. In preferred variants of such embodiments, uptake is further optimized by exploiting synergies between delivery characteristics generated by the device and by the formulation or composition of the delivered material In some embodiments, the substance comprises one or more agents to optimize delivery through the mucosal membrane by means of mucoadhesive agent and/or a permeability enhancer agent and/or a particulate formulation in the nano-particle or macro-particle range, and any combination thereof. In such embodiments, the combination of the device and substance enhance the delivery of the active agent to the target area (nasal epithelium and more specifically olfactory epithelium) and from there to the target tissue (for example the brain).

A non-limiting example is a composition comprising a drug to be delivered and at least one chemical permeation enhancer (CPE). In a preferred embodiment, the composition contains two or more CPEs which, by using a nasal delivery device, affect in an additive manner or behave synergistically to increase the permeability of the epithelium, while providing an acceptably low level of cytotoxicity to the cells. The concentration of the one or more CPEs is selected to provide the greatest amount of overall potential (OP). Additionally, the CPEs are selected based on the treatment. CPEs that behave primarily by transcellular transport are preferred for delivering drugs into epithelial cells. CPEs that behave primarily by paracellular transport are preferred for delivering drugs through epithelial cells. Also provided herein are mucoadhesive agents that enable the extension of the exposure period of the target tissue/mucus membrane to the active agent, for the enhancement of delivery of the active agent to and through the mucus membrane.

In contrast to prior-art nasal delivery devices and technologies, the devices of the present invention can produce a fine aerosol in the nasal cavity or other desired body orifice at the target area and at the location of the target tissue instead of producing the aerosol only within the device or immediately after exit from the device. Utilizing the pressure as a driving force and the air as a carrier allows the material to be released from the nozzle as a mixture of aerosol and a pre-aerosolized state. The properties of the resultant aerosol are typically dependent on the properties of the device and of the medium into which the device is discharged. The properties of the device which affect the aerosol characteristics are the delivery pressure, the volume of the delivery gas, the characteristics of its orifice and time of activate.

In some embodiments, the aerosol properties are fairly independent of the delivered substance, while, in other embodiments, the pressure, volume, orifice characteristics, and delivered substance properties can be co-optimized.

In prior-art devices the aerosol is produced in proximity exit of the device. Typically, the aerosol comprises a wide "fan" of aerosol and a low driving force. Therefore, large droplets typically deposit very close to the exit from the device, while smaller droplets tend to quickly contact the walls of the passage, so that deposition is typically predominantly close to the delivery end of the device, with little of the substance reaching desired sites deeper in the body orifice, such as the middle and superior turbinates of the nose. In the present invention the aerosol created, due to the pressurized air carrier, reaches the upper regions of the nasal cavity.

Figure 1B:
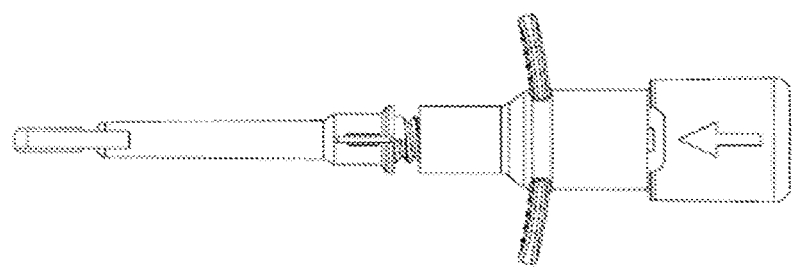

Reference is now made to FIG. 1A-B, disclosing a device according to one embodiment of the present invention. FIG. 1A shows an exploded view of the device, while FIG. 1B shows the device fully assembled. As shown in FIG. 1A, the device comprises, inter alia, a BFS nose piece (1), a pressurized-fluid container (2), an air chamber gate (3) and an activation mechanism base (4).

In the FIG. 1A, the base (4), an air chamber gate (3) has with a first gate O-ring at its proximal end and a second gate O-ring at its distal end (both shown in FIGS. 7A-7B and 8A-8E, as numerical reference 77 and 78).

The pressurized-fluid container (2) will fit over the air chamber gate (3), with the first gate O-ring and the second gate O-ring providing airtight seals before activation so that compressed gas is storable between the air chamber gate (3) and the pressurized-fluid container (2).

As will be disclosed hereinafter, the pierceable drug container (1) (e.g., BFS) in the nosepiece, where there is a puncturing element that punctures the drug container and once the compressed gas is released from the pressurized-fluid container (2), the same entrains the drug and deliver the same to the nasal cavity (see FIGS. 7A-7B and 8A-8E).

Figure 2A:
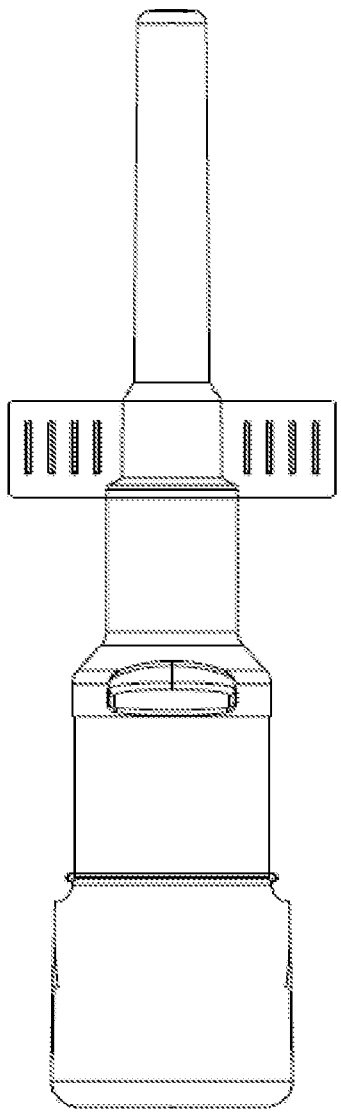
FIGS. 2A-C shows another embodiment of the present invention, with FIG. 2A showing the device, FIG. 2B showing a cross section of the device and FIG. 2C showing an enlarged view of a portion of the device.
Figure 2B:
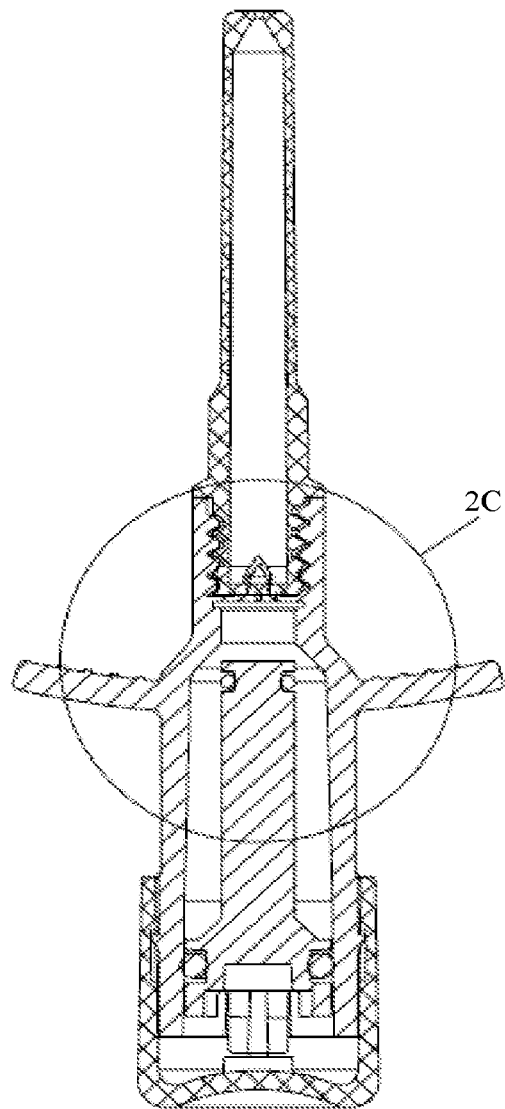
Figure 2C:
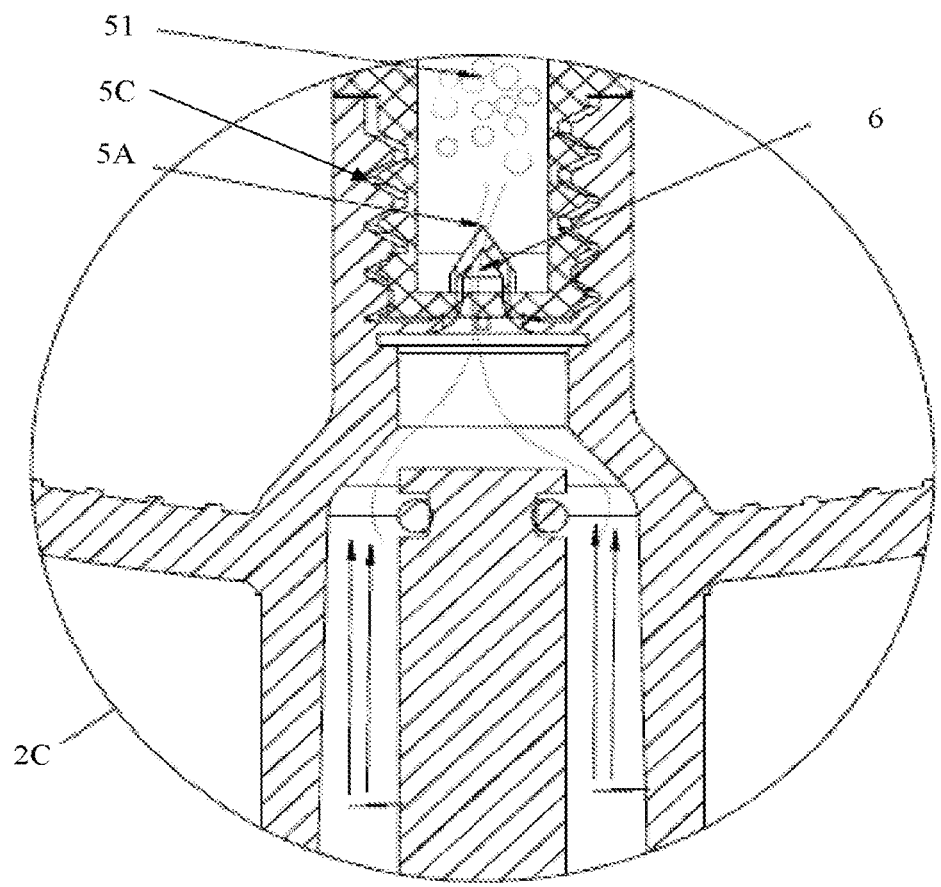

As shown in the Figs. the base of the device forms the activation button (4); to activate, the activation button (4) is pressed upward, then the air chamber gate (3) is drawn downwardly, which removes the sealing of the upper O-ring (78 in FIGS. 7A-7B). The movement of the air chamber gate (3) opens a gap between the pressurized-fluid container (2) and the BFF nose piece (1), allowing the pressurized-fluid to escape from container 2, enter BFF nose piece (1) (after the same has been pierced by the piercing needle 79, shown in FIGS. 7A-7B), and entrain the substance to the nasal cavity. Reference is now made to FIGS. 2A-C, disclosing a device according to another embodiment of the present invention. FIG. 2B depicts a cross section along the line D:D of the device as shown in FIG. 2A. The area within the circle 2C in FIG. 2B is shown enlarged in FIG. 2C, where the device's spike is disclosed (6). Also seen in FIG. 2C is a BSF lower BFS point at which the needle punctures the BFS (5A), BSF nosepiece which contain the drug (51) and an activation screw mechanism (5C).

Figure 3A:
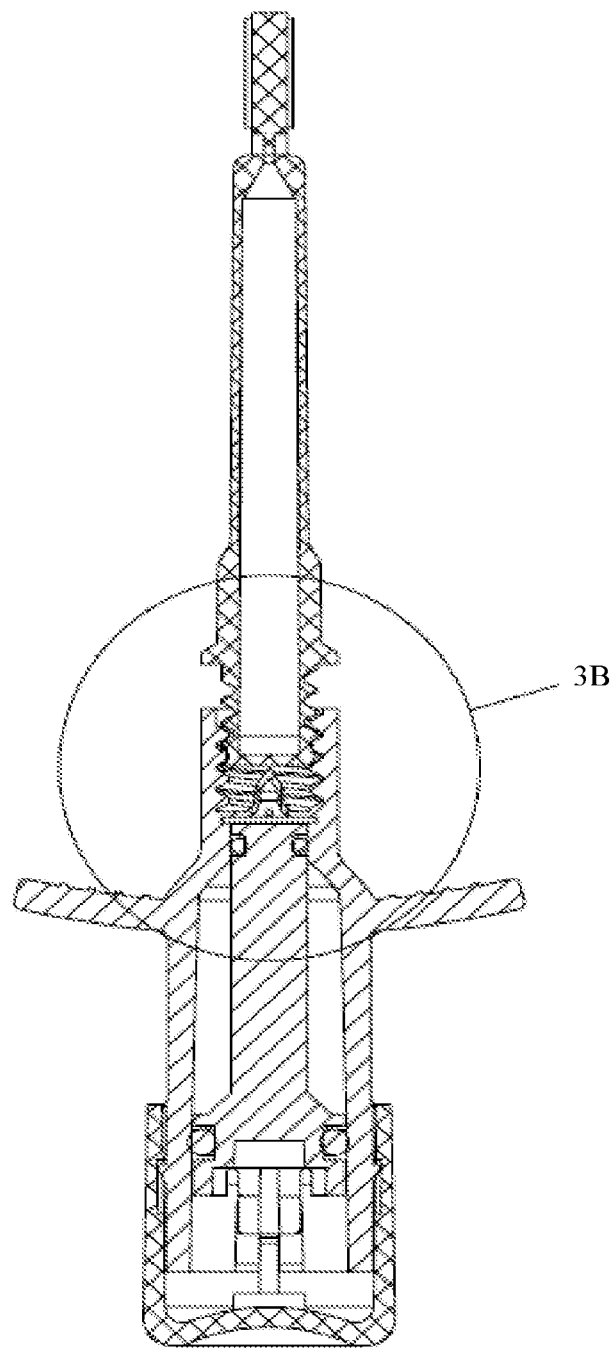
FIGS. 3A-D shows another embodiment of the present invention, with FIG. 3A showing a cross-section of the device, FIG. 3B showing an enlarged view a portion of the device, FIG. 3C showing the exterior of the nosepiece and FIG. 3D showing the device from the top.
Figure 3B:
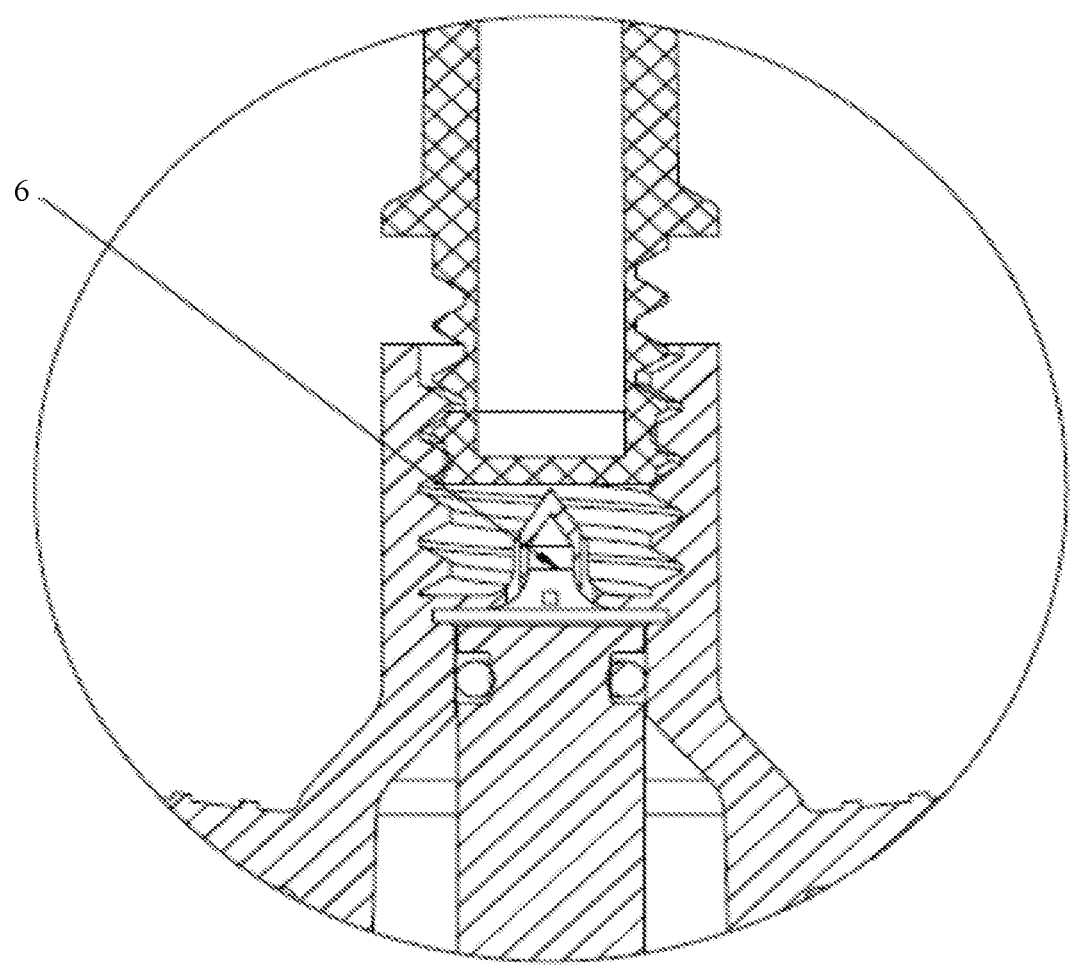
Figure 3C:
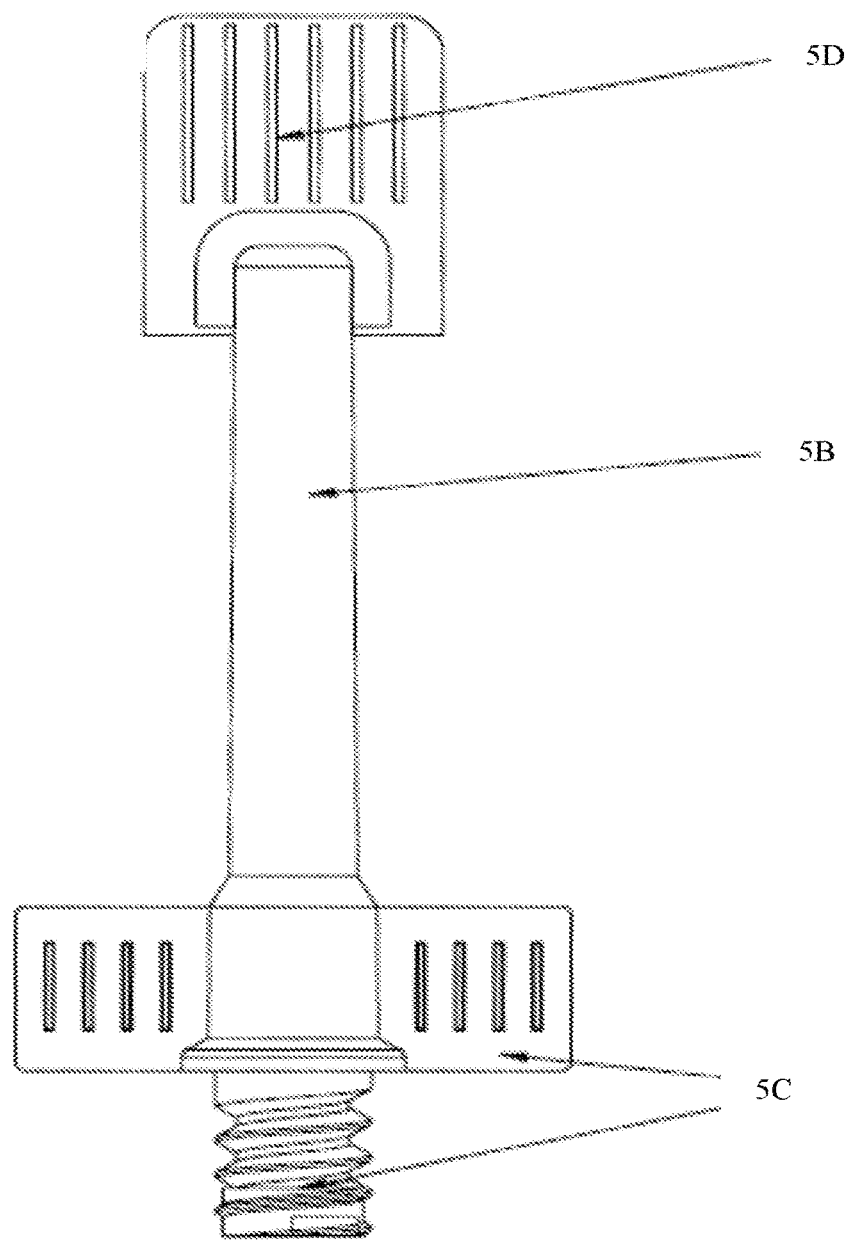
Figure 3D:
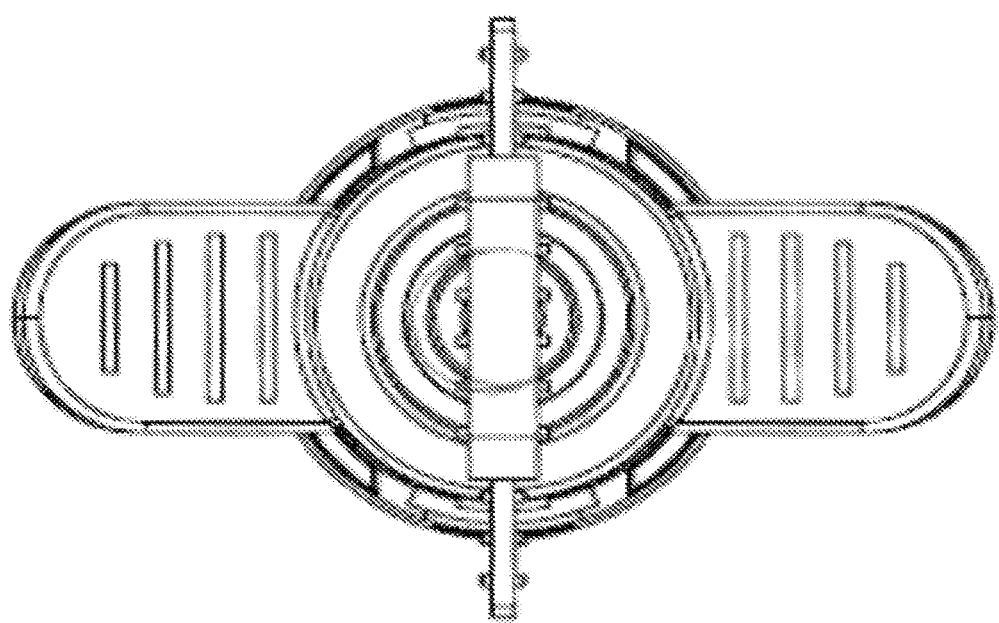

Reference is now made to FIGS. 3A-D, disclosing a device according to another embodiment of the present invention. FIG. 3A shows a cross-section of the device. FIG. 3B shows an enlarged view of the area inside the circle 3B of FIG. 3A. The piercing member (6) can be clearly seen. FIG. 3C shows the exterior of the nosepiece, showing the activation screw mechanism (5C) that is tightened in order to drive the bottom of the drug container against the spike and thereby pierce the drug container; the nosepiece cover (5D) and the main body of the nosepiece (5B). FIG. 3D shows the device from the top.

Figure 4A:
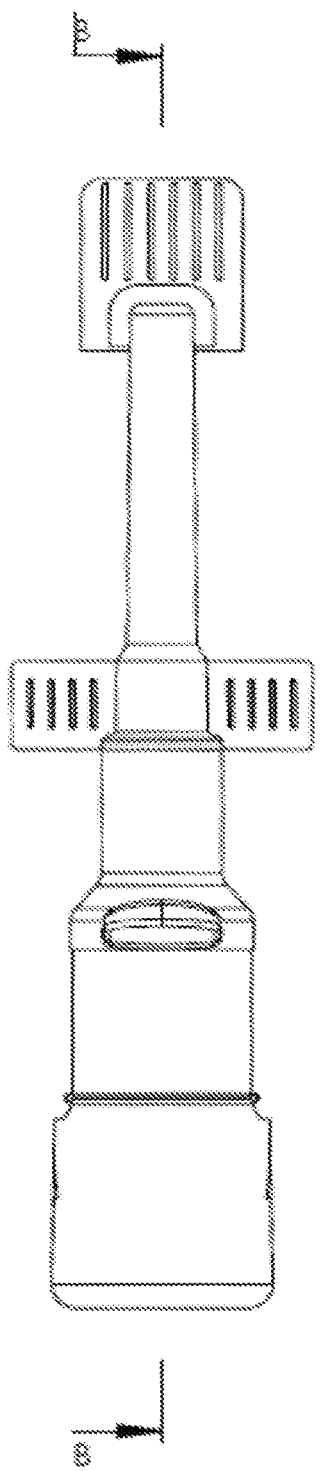
FIGS. 4A-C shows another embodiment of the present invention, after activation, with the device shown in FIG. 4A, a cross section of the device in FIG. 4B and an enlarged view a portion of the device in FIG. 4C.
Figure 4B:
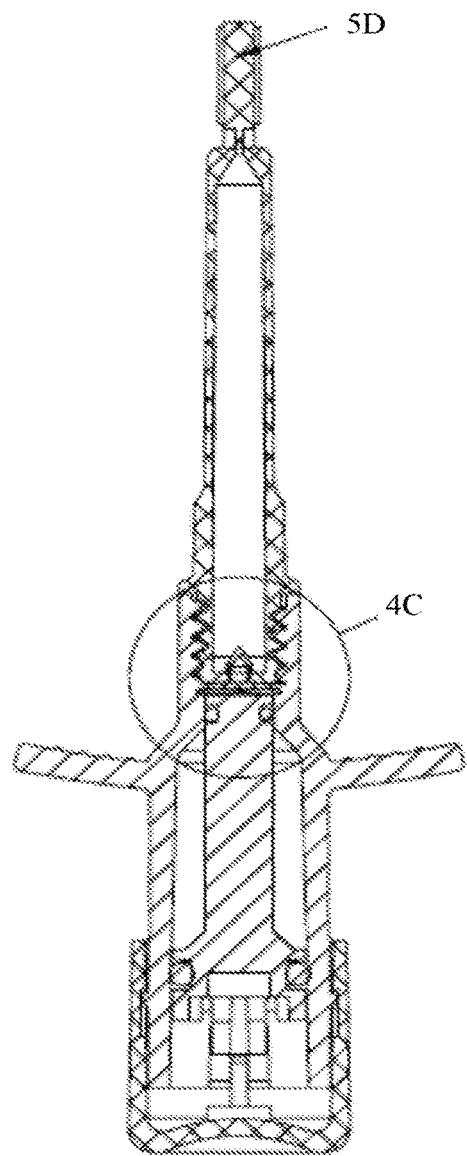
Figure 4C:
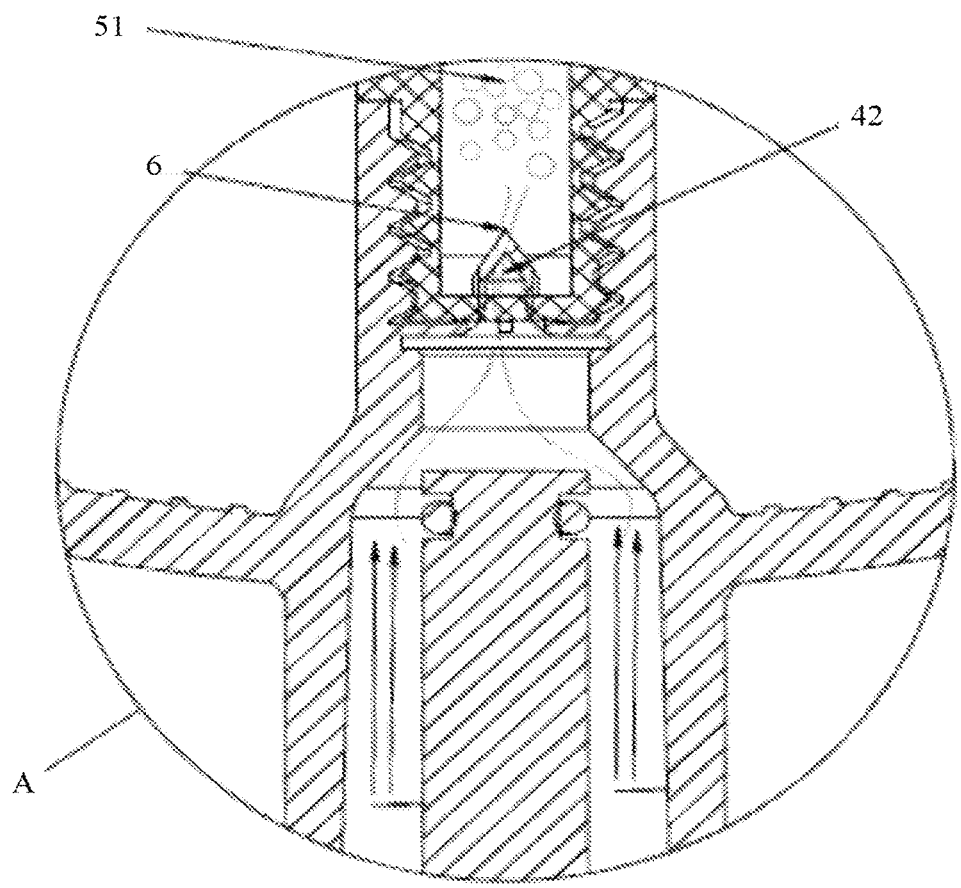

Reference is now made to FIGS. 4A-C, disclosing a device according to another embodiment of the present invention. Here a device is after the activation (FIG. 4A). FIG. 4B shows a cross section of the same along the line B:B. The area within circle 4C is shown enlarged in FIG. 4C, namely a cross section of the piercing member. Drug powder and/or liquid schematically illustrated (51). Air flow through the spike holes (42) entrains the drug.

Figure 5B:
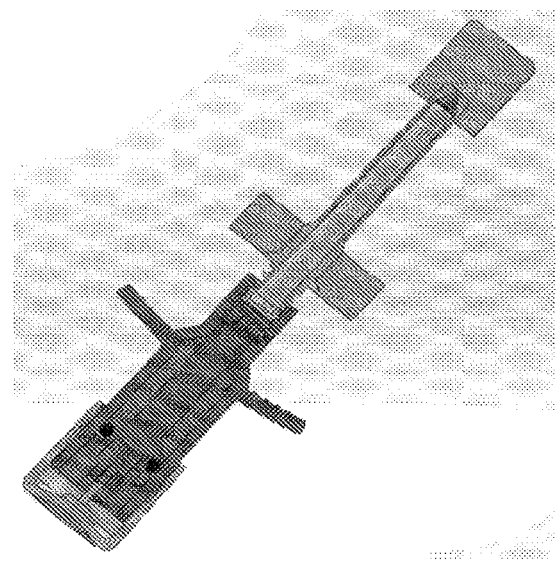
FIGS. 5A-G show another embodiment of the device, with FIG. 5A showing a side view of a pre-used device carrying a BFS, FIG. 5B showing a cross section of the same, FIGS. 5C and 5D depicting the device when connected to a BFS, FIG. 5E showing the same when the device is ready to use, FIG. 5F showing connection of the BFS to the device.
Figure 5A:
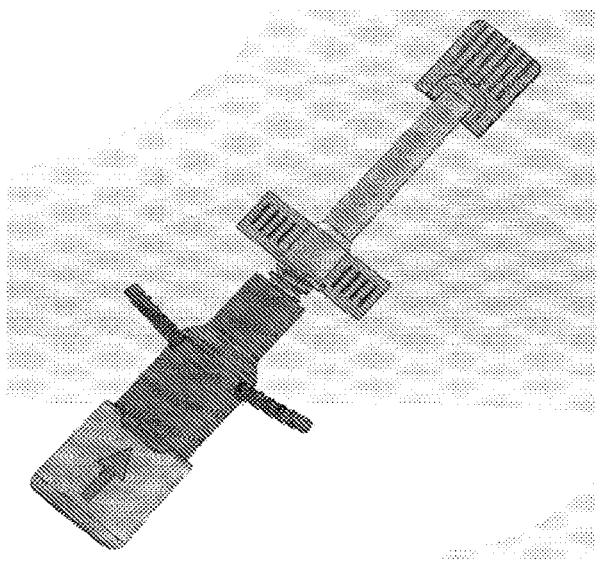
Figure 5D:
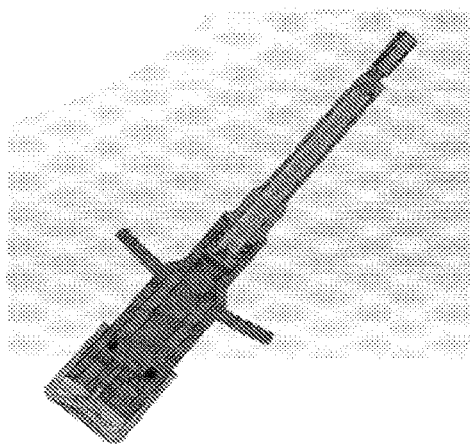
Figure 5C:
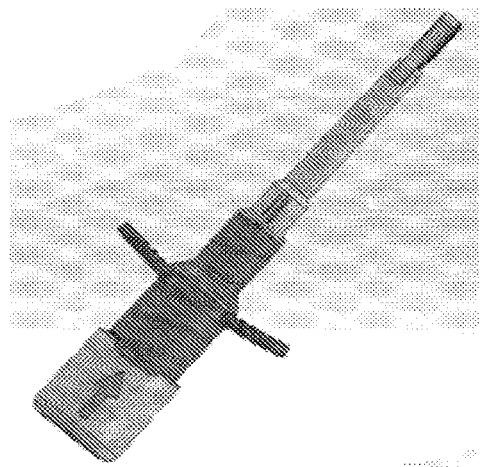
Figure 5E:
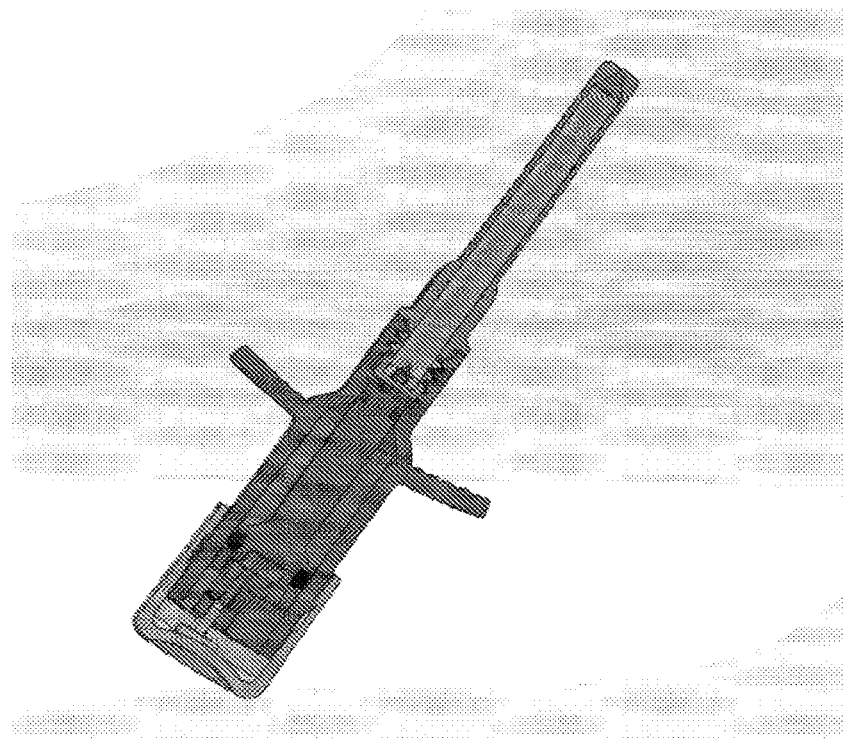
Figures 5F, 5G:
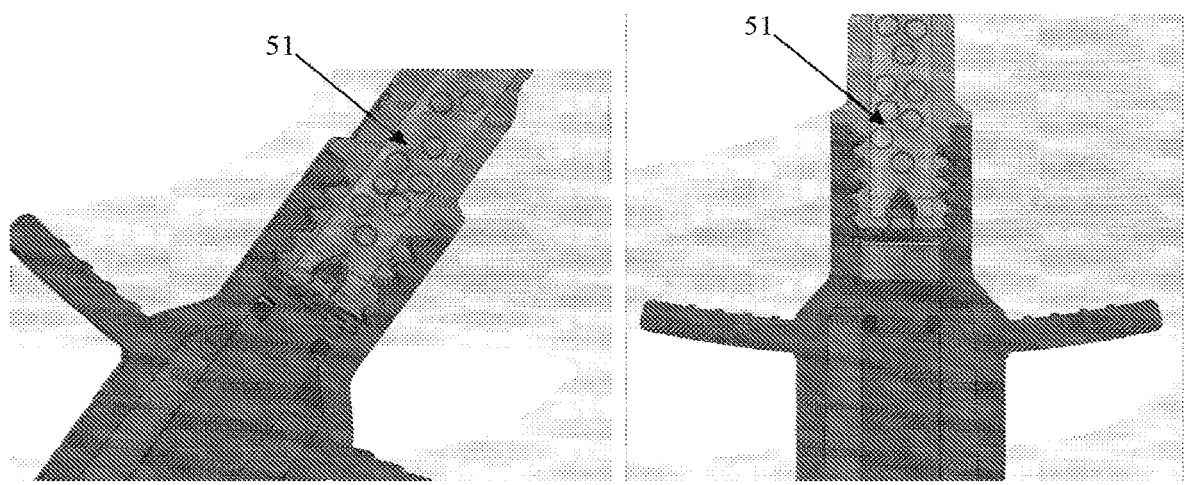

Reference is now made to FIGS. 5A-G, disclosing a device according to another embodiment of the present invention. FIG. 5A is a side view of a pre-used device carrying a BFS, and FIG. 5B is a cross section of the same. FIGS. 5C and 5D similarly depict the device when connected to a BFS. FIG. 5E shows the same when the device is ready to use, FIG. 5F illustrates the connection between the BFS to the device; drug (51) is shown. The device after activation presents the flowing drug (51) in FIG. 5G.

Figure 6B:
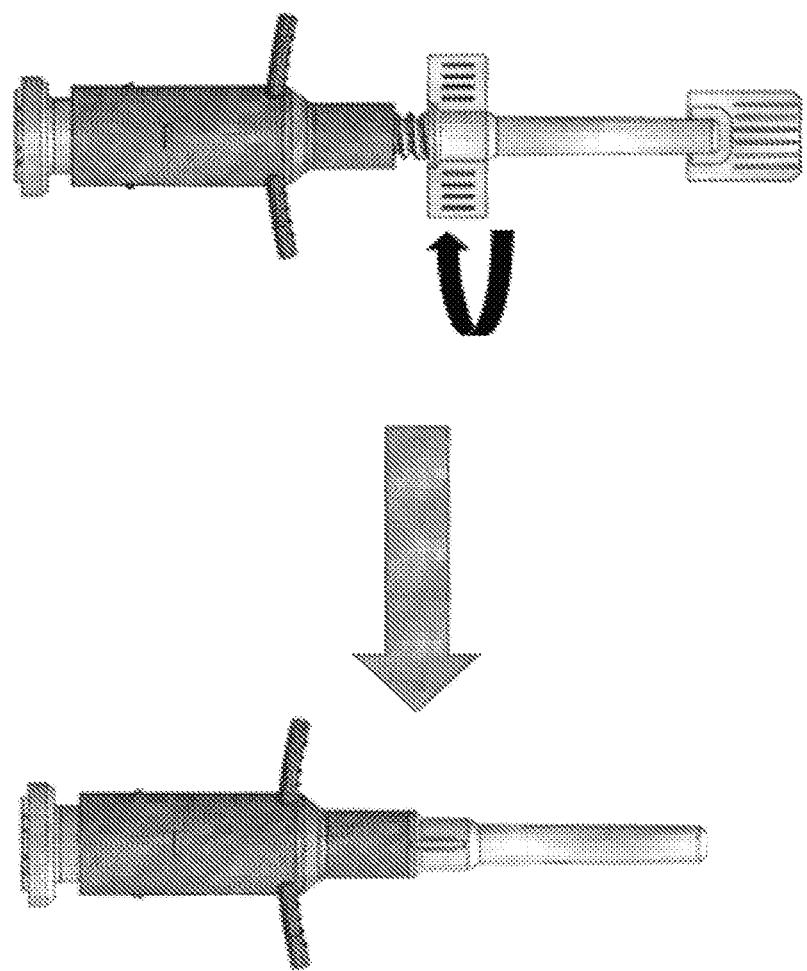
Figure 6C:
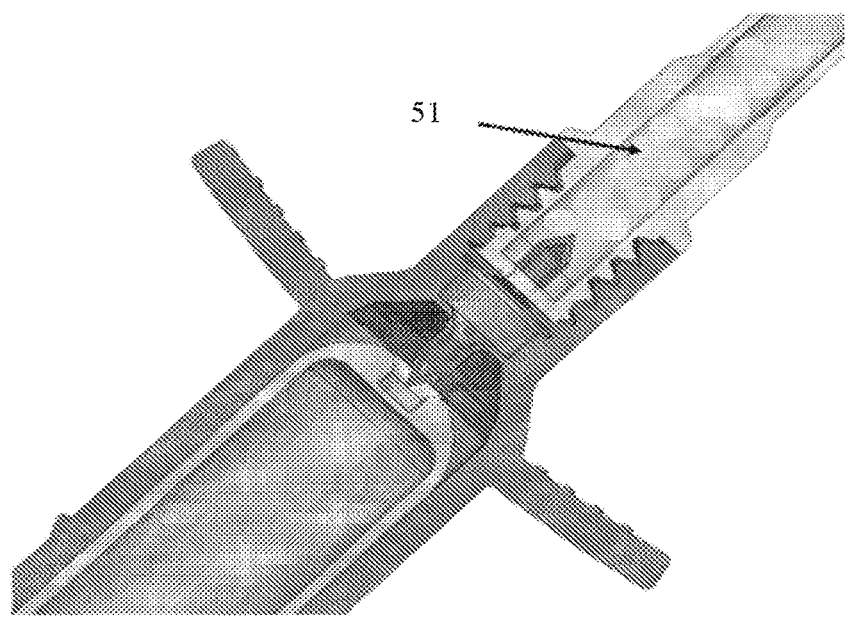
Figure 6D:
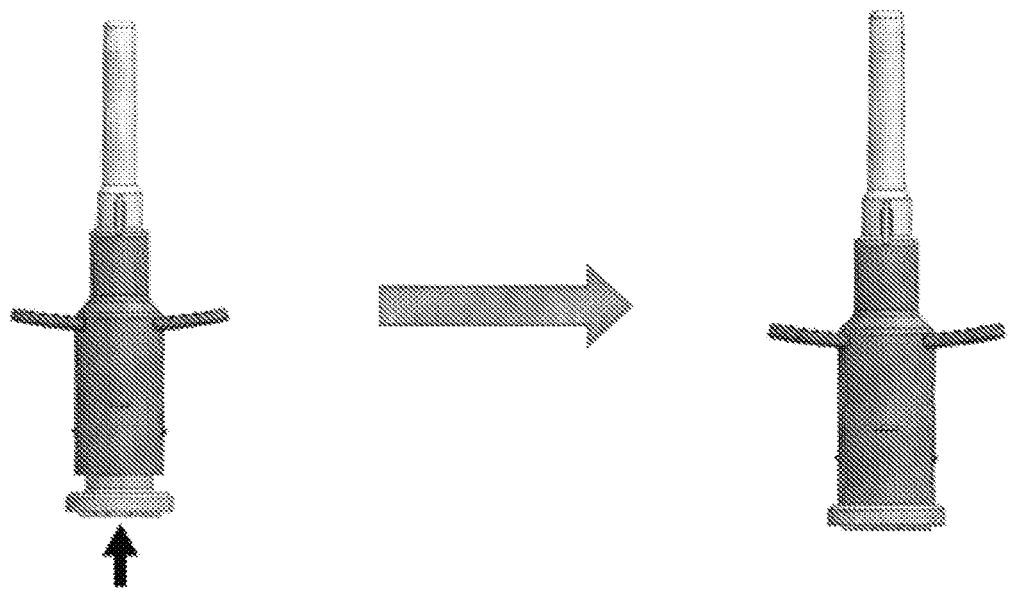
Figure 6E:
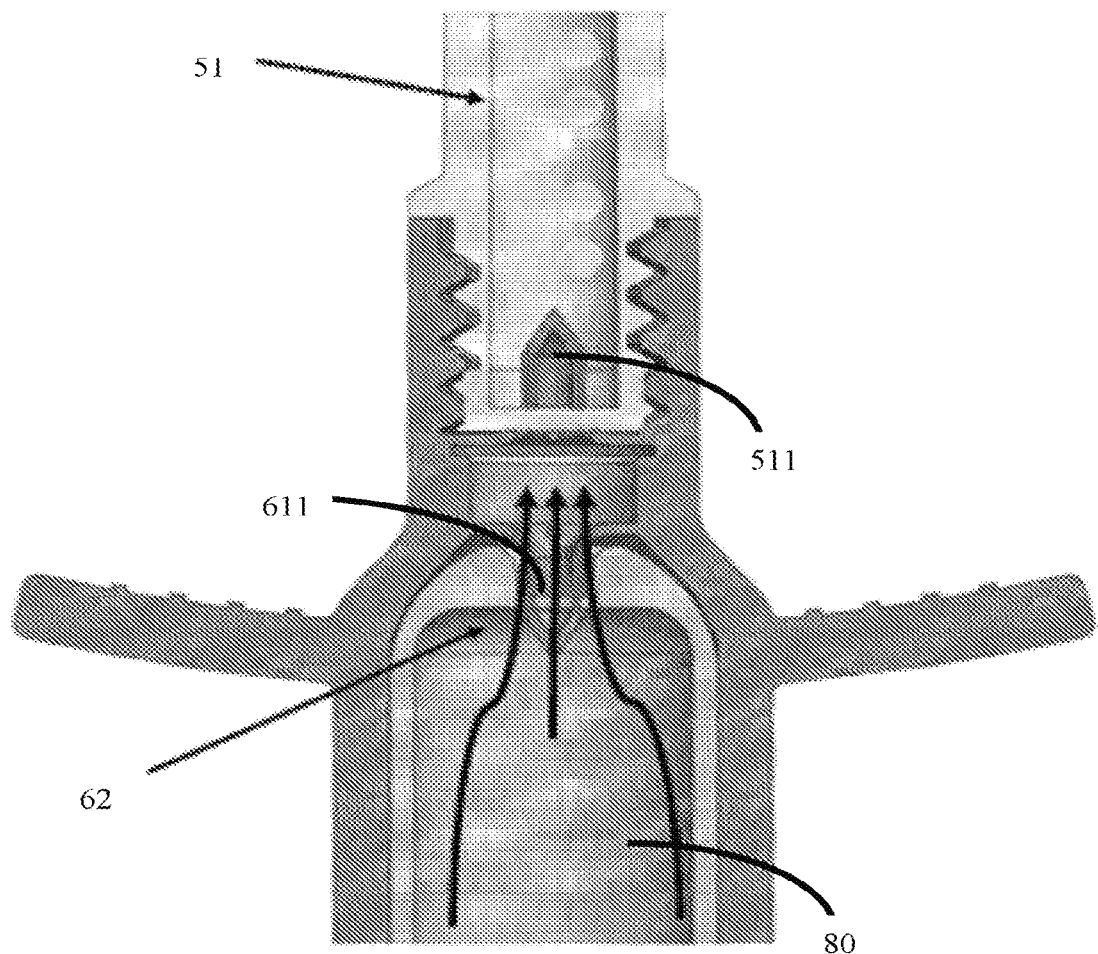

Reference is now made to FIGS. 6A-E disclosing a device according to another embodiment of the present invention. FIG. 6A illustrates a side view (image on the top) of a pre-used device carrying a BFS. Images on the middle and in the bottom are cross sections of the same, showing BFS nosepiece and BFS air container before contact. FIG. 6B shows the second step after introducing the BFS, namely securing the BFS to the device, here by turning the nosepiece of the BFS clockwise. Upon rotation of the nosepiece, the piercing member 511 (shown in FIG. 6C), pierces the drug compartment. A further step is removing (e.g., breaking) the cap, the image at the bottom presents the device after breaking the said cap. The drug (51) is presented in cross section view of FIG. 6C. In FIG. 6D, a button at the base of the device is pushed. Such push actuates the base and a second piercing member 611 pierces the container 80. Subsequently, as depicted in FIG. 6E, pressurized fluid (air, nitrogen etc.) flows from its container (62) to the drug-containing BFS and carries the drug (liquid phase, solid powder particles etc.) (51) outwardly.

One should also note that this example is shown for the same invention but with another kind of pressurized gas container and a different way of compressed gas discharge (by puncturing the container rather than the gate that is shown in the previous figures.

Reference is now made to FIG. 7A, FIG. 7B and FIGS. 8A-8E disclosing a device according to another embodiment of the present invention in a side view and exploded view, respectfully; wherein 70 is a cover holding area; 72 is a pressurized fluid container; 73 is an activation mechanism base; 74 is a cover's body; 75 is a nosepiece; 76 is an air chamber gate; 78 and 77 are O-rings; 79 is a needle; 75 is a nosepiece one way screwing mechanism; 710 is a drug's space; 712 is an air chamber gate's legs; 713 is an air chamber gate's snaps; 714 is a drug storage container locking notch; 715 is a drug storage container locking pin; 716 is an orifice-creating piercing needle; 717 is an orifice; 718 is an aerosol; 720 is a safety latch; 721 and 722 locks; 723 is a pressurized fluid container's internal screwing mechanism. The device comprises modules 70-79 and 710-720, where 71, 74, and 713, and nozzle (orifice) 717 are related with the nosepiece; 72, 76-79, 710-712, 716, to the body and module 73 and 713 is in device's operating button.

Figure 8A:
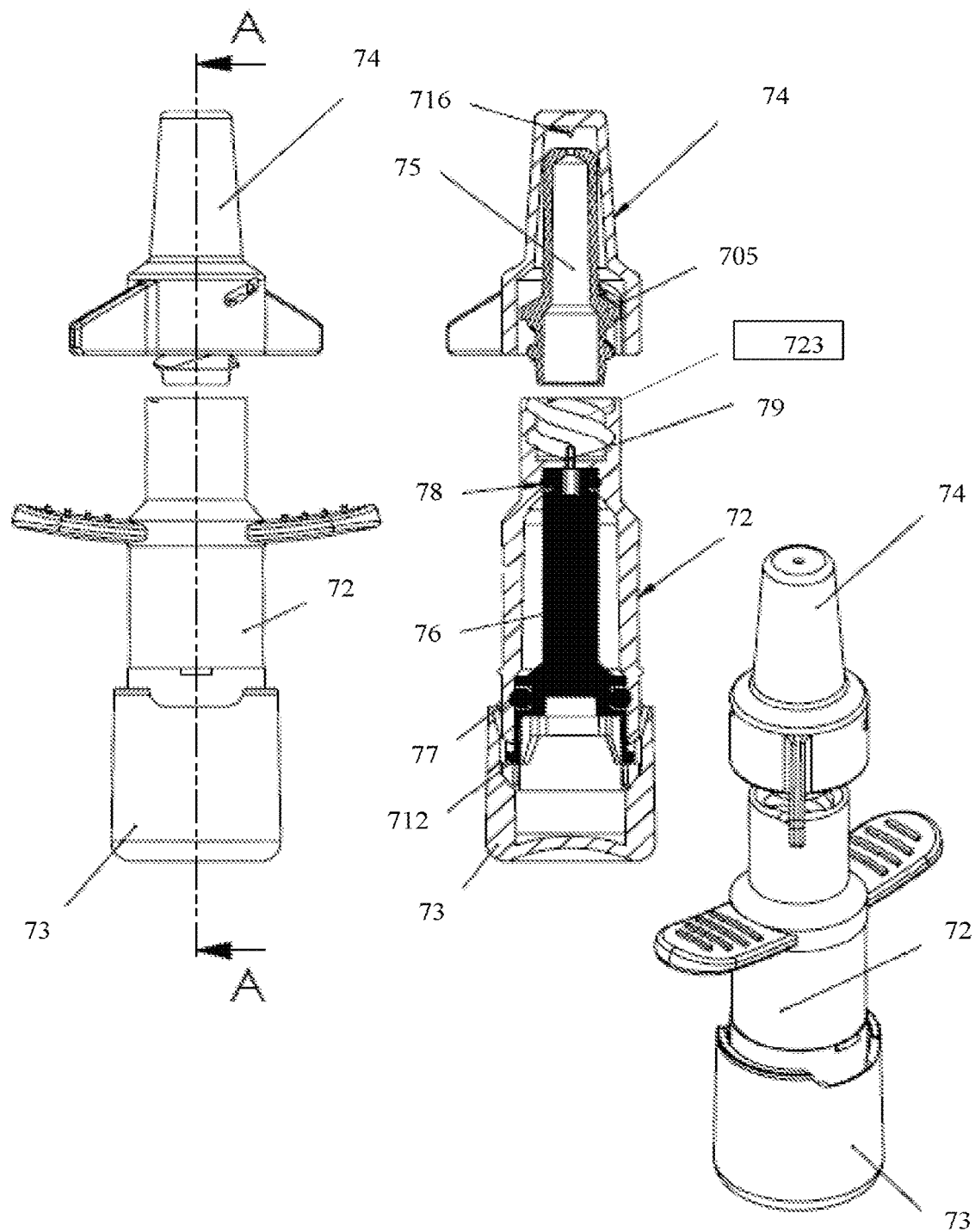
FIGS. 8A-8E shows same device in various modes of operation.
Figure 8B:
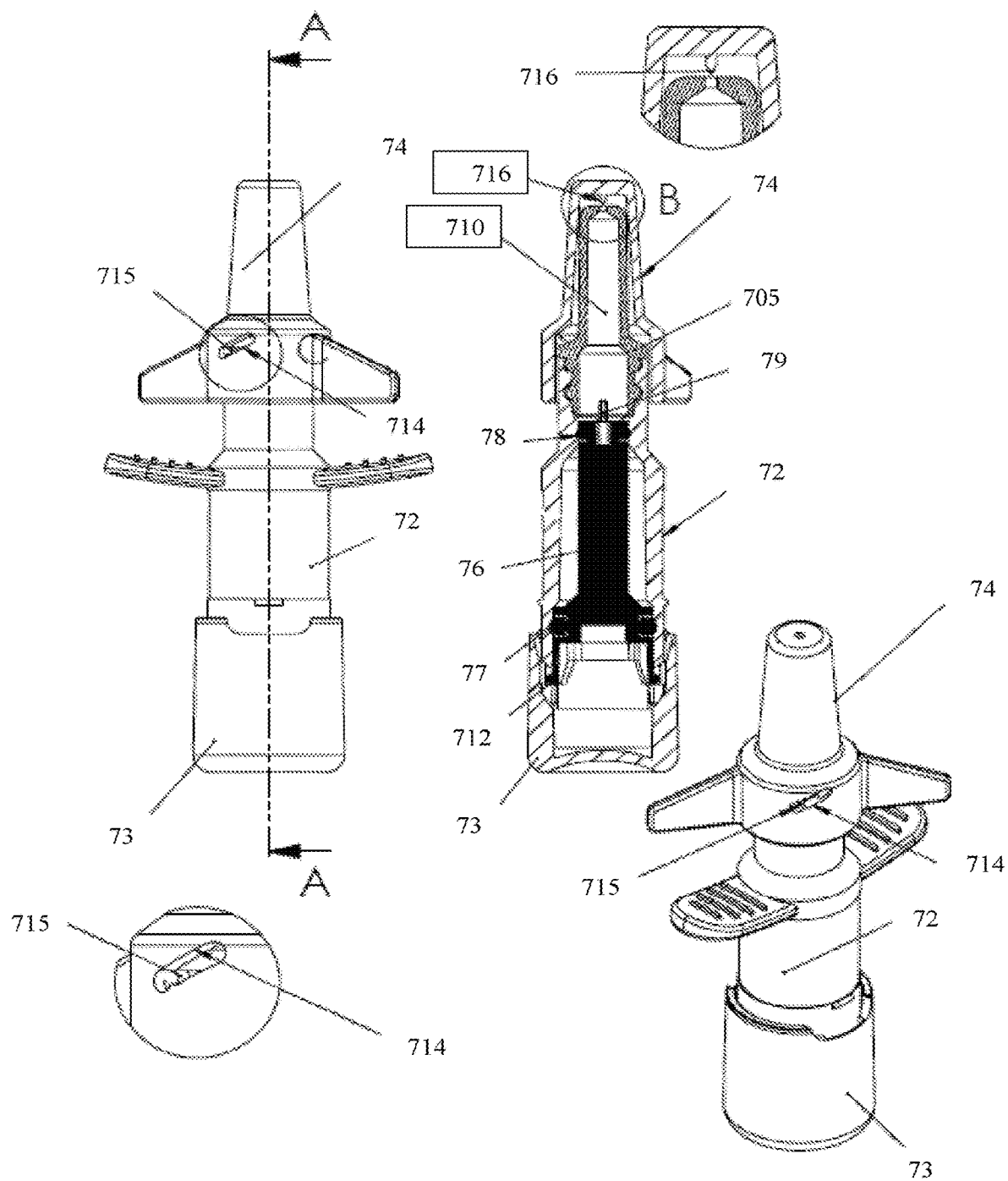
Figure 8C:
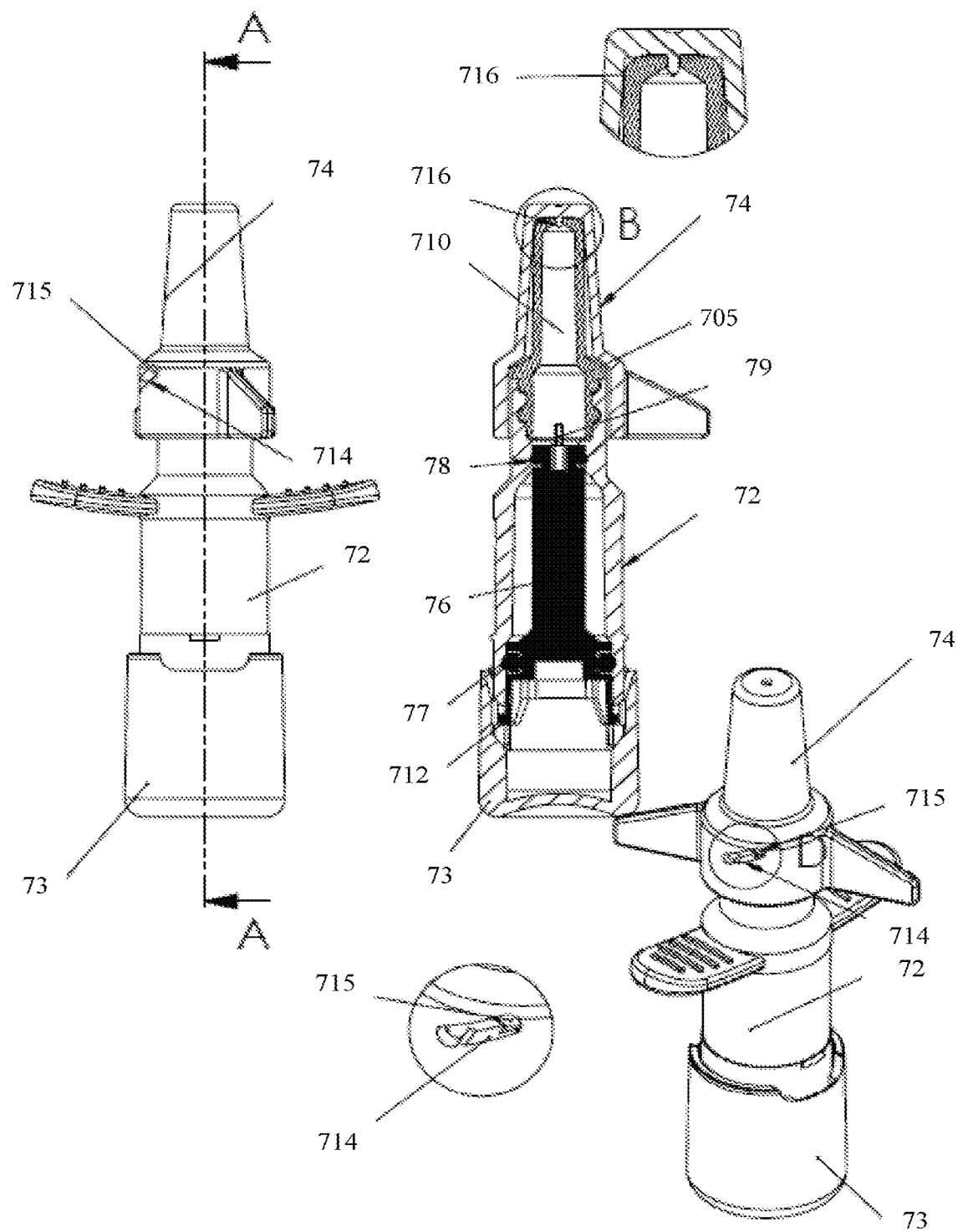
Figure 8D:
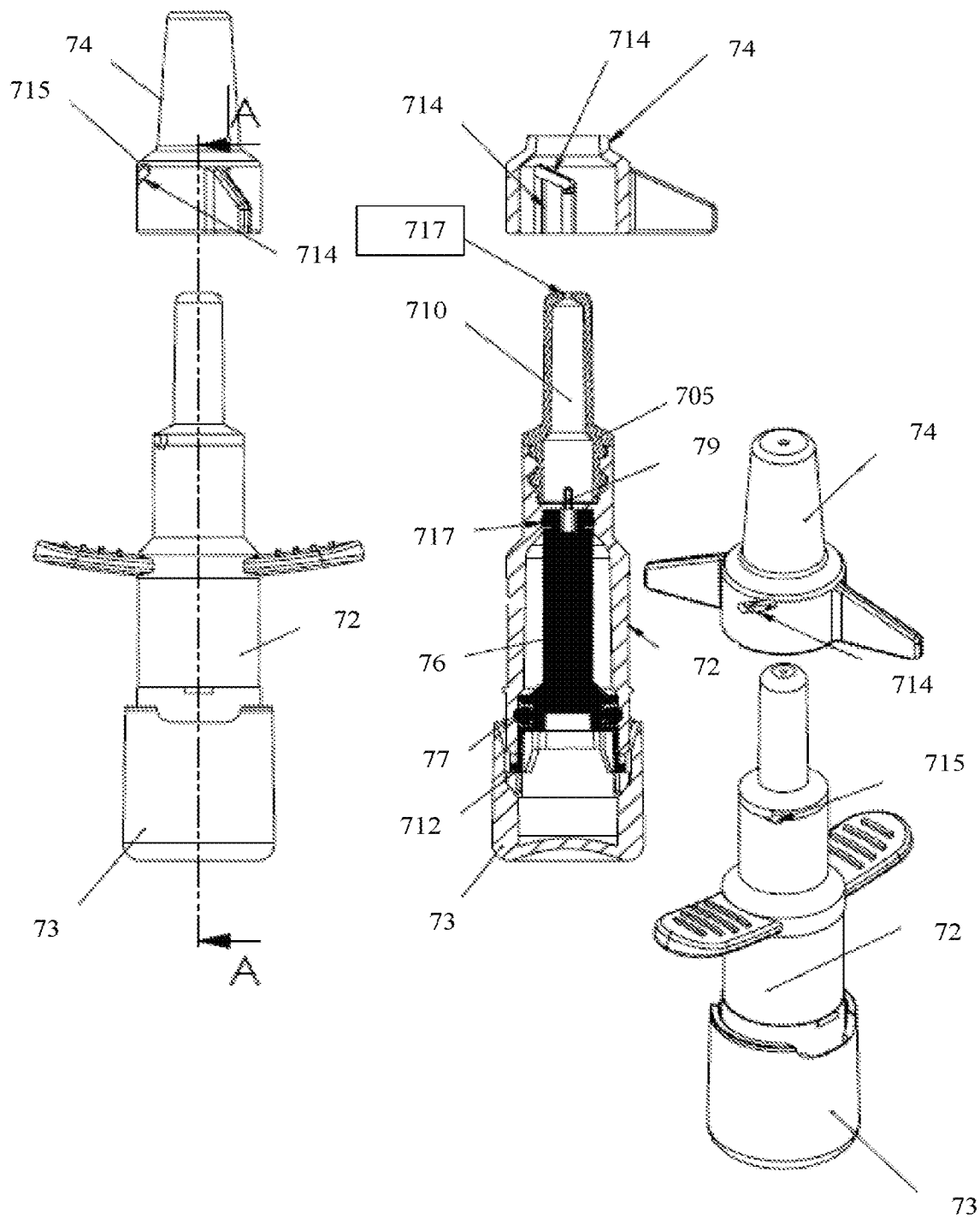
Figure 8E:
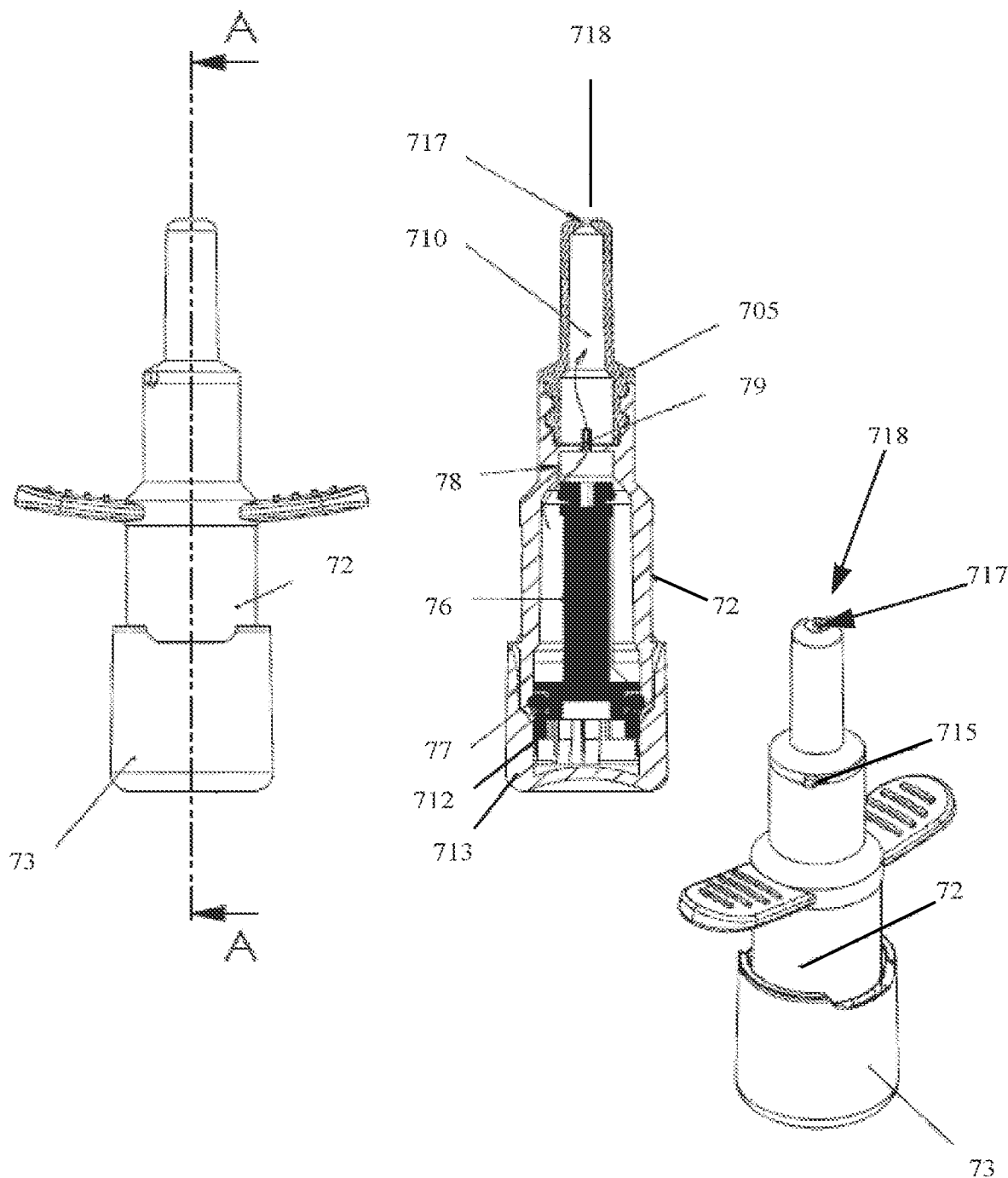

In the following sets of figures, namely FIG. 8A-8E, operation modes are illustrated, illustrating a method for delivering either one or more substances within at least one body cavity, characterized by steps of providing a vial with $V_{sub}$ [ml] of said substances; said vial selected from a pierceable container, a blow-fill-seal and a form-fill-seal, further providing said vial with a fluid inlet and a fluid discharging outlet of diameter D [mm], configured for placement in proximity to said body cavity; configuring said fluid inlet by means of size and shape to interface a puncturing member, so that upon coupling to the fluid inlet, piercing of the same, thereby providing the substances in a fluid communication, via a valve, with a chamber configured to accept pressurized fluid at volume $V_{PF}$ [ml] (or mg) and pressure $P_{PF}$ [barg]; the valve is commutable from an CLOSE to an OPEN CONFIGURATION within a short period of time, <500 milliseconds (dT); at the OPEN CONFIGURATION, facilitating the flow of the pressurized fluid to from the chamber, via the fluid inlet, entraining the substances; and then erupting via the fluid discharging outlet to within the body cavity, such that the release time of the $V_{sub}$ [ml or mg] of the substances and the $V_{PF}$ [ml] of the pressurized fluid, $dT_{release}$ is less than 500 milliseconds. Each pf the figures comprises a front view (left side), cross-section (A:A, middle) and isometric view (right side). FIGS. 8B and 8C further depict a rotation mechanism 714-715, which allows a rotation (here, ¼ rotation) thereby enabled the piercing of the nosepiece substance container.

According to another embodiment, the rotation results in a double piercing of the nosepiece substance container and the pressurized air container.

According to another embodiment the pressurized air container is sealed by means of at least one O-ring, such that movement of the o-ring removes the sealing and enables the release of the pressurized air. In some embodiment at least 2 o-rings are used. One o-ring at the bottom of the pressurized air container and the second at the upper portion of the pressurized air container to seal and separate between the pressurized air container and the nosepiece substance container.

At final step (FIG. 8E), upon pressing the activation mechanism base 73, results in movement of the air chamber gate 76 and the upper o-ring to thereby enable the release of the pressurized air from the pressurized air container and into the nosepiece substance container to entrain the same. Once the pressurized air entrains the substance, aerosol 718 is provided throughout the orifice 717, having a narrow plume angle (θ). It is in the scope of the invention wherein the cover comprises means to protect the drug from UV, e.g., photoprotective agents, such as oxybenzone, titanium oxide and octyl methoxycinnamate.

Figure 9:
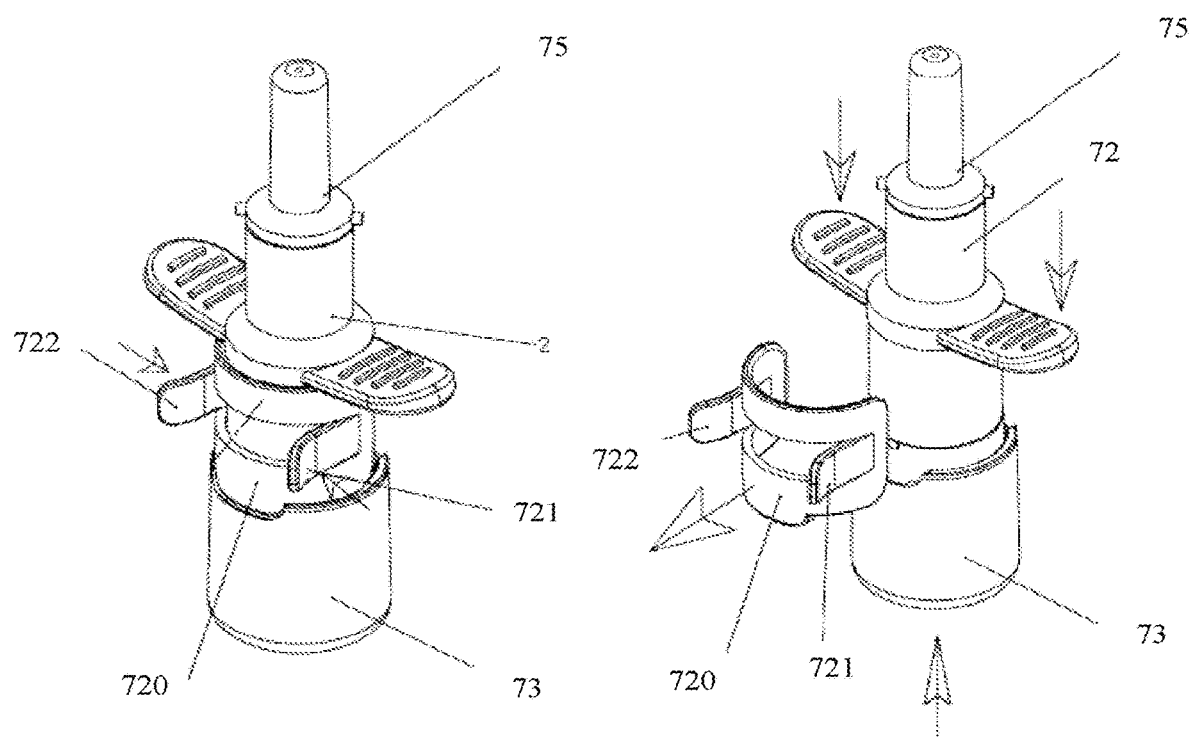
FIG. 9 depict two views of the device interconnected to a safety latch according to an embodiment of the present invention.

Reference is now made to FIG. 9 disclosing a device according to another embodiment of the present invention, where the device comprises a safety latch 720 with its two locks 721-722, configured to avoid undesired or accidental operation of the device, i.e., by pressing activation mechanism base 73 and pressurized fluid container (body) 72.

It is well in the scope of the invention wherein the pressurized fluid is accommodated within container for a respectively long time, e.g., by having a pre-pressurized container (step 1A) in a fluid connection (step 2A) with the BFS and releasing the same (step 3A), or alternatively a container suitable to pressuring the fluid in situ within the container, e.g., by introducing a pump or piston mechanism that pressuring ambient air to the container in a first step (step 1B) and accommodating the pressurized fluid along a relatively short time of step 2B, then free the fluid to flow in step 3B.

It is well in the scope of the invention wherein at least one of the steps 1A to 3A, 1B to 3B is provided in an intermittent manner, e.g., by train of n pulses, n is an integer equals to being greater than 2, e.g., 2, 5, 10, 30 or more. Pulses are provided by various mechanisms selected in a non-limiting manner from a series of pressuring efforts (pulsated piston for example and/or series of volume changes within the container); series of releasing pressurized fluid flow, by having rapid open/closed shutting actions of the valve and/or applying blowable lips or rid(s) at the end of the orifice, e.g., as those provided in a mouthpiece of a wind instruments.

The pulses can be identical, e.g., same pressure, same period of time, same volume etc. Additionally, or alternatively, some of pulses can be different by means of e.g., pressure, time, volume etc. It is well in the scope of the invention wherein the fingerprint of the pulses is of increasing pressure, increasing time; and/or increasing pressure decreasing time; and/or decreasing pressure same time and so on and so forth.

The device of the present invention is provided useful for treatment of various indications defined below, by their efficient medicaments provided herein in a non-limiting manner:

Example 1

Treatment of allergic rhinitis is found useful by utilizing a device of the present invention for the delivery of anti-histamines and/or gluco-corticosteroids.

Example 2

Treatment of Cough & Cold is found useful by utilizing a device of the present invention for the delivery of various medicaments, some are defined above in the substances list.

Example 3

Treatment of pain & central nervous system is found useful by utilizing a device of the present invention for the delivery of various medicaments; e.g., treatment of chronic conditions such as Alzheimer's, Parkinson's, Depression, pain, seizures, epilepsy and acute migraine, conscious sedation and sleep aids.

Example 4

Treatment of vaccines, immunotherapy and anti-viral agents are found useful by utilizing a device of the present invention for the delivery of various medicaments, some are defined above in the substances list.

Example 5

Treatment of asthma and COPD is found useful by utilizing a device of the present invention for the delivery of various medicaments, some are defined above in the substances list.

By the device disclosed herein, the pre-aerosolized mixture of gas and substance exits the device with a significant driving force as a mixture of aerosol and pre-aerosolized material (fluid or powder). When the pre-aerosolized material hits the walls of the nasal passages, it "explodes" into a fine aerosol that is capable of being driven by the pressure deep into the nasal passages to deposit in the desired region.

Examples 6

Rectal, trans anal and/or trans rectal administration of cannabis oil see treatment in US20190247632, is provided useful by the device presented herein. Rectal and vaginal suppositories have both been used to deliver medicine to patients for decades. Use of the device herein is effective in intravaginal and intra-annal administration of THC, provided in methods adapted from the art, see GROVE, JELENA, and ON JULY. "PROJECT CBD: DO CANNABIS SUPPOSITORIES WORK? And Elsohly, Mahmoud A., et al. "Rectal Bioavailability of Delta-9-Tetrahydrocannabinol (cannabis-terms tetrahydrocannabinol) from Various Esters." Pharmacology Biochemistry and Behavior, vol. 40, no. 3, 1991, pp. 497-502.

Intravaginal device as herein disclosed is useful for delivery of an antifungal, antiviral, antibacterial, trichomonicidal and parasiticidal pharmaceutical agent intravaginally to a female vagina and transvaginally to uterus and general circulation through a vaginal mucosa. Hence, the device is especially useful is administrating miconazole, terconazole, isoconazole, fenticonazole, fluconazole, nystatin, ketoconazole, clotrimazole, butoconazole, econazole, tioconazole, itraconazole, 5-fluoracil and metronidazole, and the antiviral agent selected from the group consisting of acyclovir, femciclovir, valacyclovir and AZT, and the antibacterial agent selected from the group consisting of clindamycin, tetracycline, amoxicillin, ampicillin, erythromycin, doxycycline, lumefloxacin, norfloxacin, afloxam, ciproflaxin, azitromycin and cefitoxine present in amount from about, and the antichlamydial agent selected from the group consisting of tetracycline, doxycycline and erythromycin; and the trichomonicidal and parasiticidal agent selected from the group consisting of metronidazole and clotrimazole in methods adapted from U.S. Pat. No. 6,416,779.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for delivering either one or more substances within at least one body cavity, characterized by at least one pierceable vial comprising $V_{sub}$ [ml or mg] of said one or more substances; said at least one vial having at least one fluid inlet port of diameter $D_{in}$ [mm] and at least one fluid discharging outlet port of diameter $D_{out}$ [mm], configured for placement in proximity to said at least one body cavity; said at least one fluid inlet port configured by means of size and shape to interface with at least one puncturing member, configured to, upon coupling to said at least one fluid inlet port, piercing the at least one fluid inlet port, thereby providing said one or more substances in a fluid communication with at least one chamber configured to accept pressurized fluid at volume $V_{PF}$ [ml] and pressure $P_{PF}$ [barg]; said pressurized fluid is configured to flow from said at least one chamber, via said at least one fluid inlet port, entrains said one or more substances, erupts via said at least one fluid discharging outlet port to within said at least one body cavity in the form of aerosol, such that a release time of said $V_{sub}$ [ml or mg] of said one or more substances and said $V_{PF}$ [ml] of said pressurized fluid, $dT_{release}$ is less than 500 milliseconds; wherein a) $V_{PF}$ is in a range of 1 to 50 ml;
b) $V_{sub}$ is in a range of a bout 0.01 to a bout 7 ml;
c) $P_{PF}$ is in a range of up to about 10 barg;

further wherein at least one of the following is being held true:

d) $D_{in}$ or $D_{out}$ are in a range of 0.2 to 6 mm;
e) a pressure velocity of the pressurized fluid is greater than 0.001 barg/ms;
f) said pressure velocity is greater than 0.01 barg/ms;
g) a volume rate $dV_{sub}/dT_{release}$ of the pressurized fluid is greater than 0.0001 ml/ms;
h) said volume rate $dV_{sub}/dT_{release}$ is greater than 0.001 ml/ms;
i) a volume rate $dV_{PF}/dT_{release}$ is greater than 0.001 ml/ms;
j) said volume rate $dV_{PF}/dT_{release}$ is greater than 0.01 ml/ms;
k) any combination thereof;

further wherein said at least one vial selected from a group consisting of a pierceable container, a blow-fill-seal and a form-fill-seal;

the device further comprising at least one plunger enclosed within said at least one chamber, said at least one plunger comprising at least one sealing member adapted to seal said at least one chamber and to prevent flow of said pressurized fluid, wherein linear movement of said at least one plunger moves said at least one sealing member and creates a gap through which said pressurized fluid exits said at least one chamber.

2. The device of claim 1, wherein said at least one puncturing member is adapted to pierce said at least one vial by means of a screw mechanism, such that rotation of a nosepiece cover along said screw mechanism in a base enables said pierce of said at least one fluid inlet port in said at least one vial by means of said at least one puncturing member.

3. The device of claim 1, wherein said at least one sealing member is at least one o-ring adapted to seal said at least one chamber.

4. The device of claim 1, wherein said at least one chamber is a container adapted to hold said pressurized fluid at said $P_{PF}$ for prolong periods of time.

5. The device of claim 1, wherein said at least one vial is made of at least one material selected from a group consisting of high- or low-density polyethylene, high- or low-density polypropylene and any combination thereof.

6. The device of claim 1, wherein at least one of the following is true:

l) said at least one body cavity is selected from a group consisting of nasal cavity, the mouth, the throat, an ear, the vagina, the rectum, the urethra, and any combination thereof;
m) a pressurized gas is selected from a group consisting of air, nitrogen, oxygen, carbon dioxide, helium, neon, xenon and any combination thereof;
n) during dispensing of said one substance one or more substances, a mixture of a predetermined volume $V_{gas}$

[ml] of said pressurized gas with a predetermined volume $V_{sub}$ [ml or mg] of said one or more substances entrained within it forms a plume of aerosol; said aerosol having a predetermined distribution, said distribution being either homogeneous or heterogeneous, said heterogeneous distribution is selected from a group consisting of: an arbitrary distribution, a distribution in which the density of said one or more substances within said mixture follows a predetermined pattern, and any combination thereof; characteristics of said aerosol selected from a group consisting of: particle size, particle shape, particle distribution, and any combination thereof, are determinable from characteristics of said device selected from a group consisting of: said predetermined volume of said pressurized gas, said predetermined volume of said one or more substances, said predetermined pressure of said pressurized gas, said predetermined orifice size, and any combination thereof;

o) one or more substances is selected from a group consisting of a gas, a liquid, a powder, an aerosol, a slurry, a gel, a suspension and any combination thereof;

p) one or more substances is stored under either an inert atmosphere or under vacuum to prevent reactions during storage;

q) a dose-response curve is substantially linear for brain concentration of said one or more substances when administered nasally via said device; and r) a dose-response curve for brain concentration having a fit selected from a group consisting of logarithmic, parabolic, exponential, sigmoid, power-low, and any combination thereof; of said one or more substances when administered nasally via said device.

7. The device of claim 1, wherein said pressurized fluid entrains said one or more substances in a pulsed manner, such that a plurality of portions $V_{PF}$ are configured to erupt via said at least one fluid discharging outlet port into said at least one body cavity.

8. The device of claim 1, further comprising a safety latch, adapted to prevent accidental operation of said device.

9. The device of claim 1, wherein said one or more substances is selected from a group consisting of proteins; stem-cells; cells, organs, portions, extracts, and isolations thereof; macro-molecules; RNA or other genes and proteins-encoding materials; neurotransmitters; receptor antagonists; hormones; Ketamine; Glucagon; substrates to treat one of the followings: anaphylaxis, Parkinson, seizures and opioid overdose; epinephrine; atropine; metoclopramide; Naloxone; Esketamine; edaravone; valbenazine; deutetrabenazine; ocrelizumab; safinamide; nusinersen; daclizumab; pimavanserin; aripiprazole lauroxil; cariprazine; brexpiprazole; eslicarbazepine acetate; flutemetamol F18 injection; vortioxetine; dimethyl fumarate; gadoterate meglumine; Antibody mediated brain targeting drug delivery including aducanumab, gantenerumab, bapineuzumab, solanezumab, ofatumumab CD20, BIIB033, LCN2, HMGBI; insulin; oxytocin; orexin-A; leptin; benzodiazepine i.e. midazolam; naloxone; perillyl alcohol; camptothecin; phytochemicals including curcumin and chrysin; nucleotides; olanzapine; risperidone; Venlafaxin; GDF-5; zonisamide; ropinirole; plant-originated and synthetically-produced terpenes and cannabinoids, including THC and CBD; valproric acid; rivastigmine; estradiol; topiramate or an equivalent preparation comprising CAS No. 97240-79-4; MFSD2 or MFSD2A or sodium-dependent lysophosphatidylcholine symporter; and any esters, salts, derivatives, mixtures, combinations thereof, with or without a carrier, liposomes, lyophilic or water-miscible solvents, surfactants, cells, cells fractions, at a therapeutically effective concentration.

10. A device for delivering either one or more substances within at least one body cavity, comprises a base and a nosepiece;

said nosepiece comprises:
(i) at least one pierceable vial comprising $V_{sub}$ [ml or mg] of said one or more substances; said at least one vial having at least one fluid inlet port of diameter $D_{in}$ [mm] and at least one fluid discharging outlet port of diameter $D_{out}$ [mm], configured for placement in proximity to said at least one body cavity;
(ii) a nosepiece cover configured by means of size and shape to cover at least partially said nosepiece;

said base comprises:
(i) at least one chamber configured to confine pressurized fluid at volume $V_{PF}$ [ml] and pressure $P_{PF}$ [barg];
(ii) at least one puncturing member; said at least one fluid inlet port of said at least one vial configured by means of size and shape to interface with said at least one puncturing member;

wherein actuation of said nosepiece cover configured to enable piercing of said at least one vial in said at least one fluid inlet port, by means of said at least one puncturing member;

further wherein said volume $V_{PF}$ [ml] of said pressurized fluid at pressure $P_{PF}$ [barg] is configured to be released from said at least one chamber within a short period of time, <500 milliseconds (dT), via said at least one fluid inlet port, entrains said one or more substances, erupts via said at least one fluid discharging outlet port into said at least one body cavity, such that a release time of said $V_{sub}$ [ml or mg] of said one or more substances and said $V_{PF}$ [ml] of said pressurized fluid, $dT_{release}$ is less than 500 milliseconds.

11. The device of claim 10, wherein said nosepiece cover and said nosepiece are coupled to each other.

12. The device of claim 11, wherein said coupling between said nosepiece cover and said nosepiece is reversible.

13. The device of claim 10, wherein removal of said nosepiece cover is obtained by at least one action selected from a group consisting of sliding said nosepiece cover along said device, rotating said nosepiece cover around said device, rotating said nosepiece cover around a hinge on the exterior of said device and any combination thereof.

14. The device of claim 10, wherein said nosepiece cover comprises at least one nosepiece puncturing member adapted to pierce said at least one vial to enable said at least one fluid discharging outlet port.

15. The device of claim 10, wherein said nosepiece comprises at least one port through which said one or more substances exits said device, such that said nosepiece cover seals said at least one port and removal thereof removes said seal.

16. The device of claim 10, wherein said at least one vial is selected from a group consisting of: a pierceable container, a blow-fill-seal and a form-fill-seal.

17. The device of claim 10, wherein said actuation of said device is performed by means of rotation of said nosepiece cover over said base.

18. The device of claim 17, wherein said rotation is of at least 10 degrees.

19. The device of claim 10, wherein said at least one puncturing member is adapted to pierce said at least one vial by means of a screw mechanism, such that rotation of said nosepiece cover along said screw mechanism in said base enables said pierce of said at least one fluid inlet port in said at least one vial by means of said at least one puncturing member.

20. The device of claim 10, wherein said at least one chamber is a container adapted to hold said pressurized fluid at said $P_{PF}$ for prolong periods of time.

21. The device of claim 10, additionally comprising an activation mechanism adapted to enable the release of said pressurized fluid out of said at least one chamber.

22. The device of claim 21, wherein said at least one puncturing member comprises a plurality of holes through which said pressurized fluid exits said at least one chamber and entrains said one or more substances, after activation of said activation mechanism.

23. The device of claim 10, wherein said at least one vial is made of at least one material selected from a group consisting of high- or low-density polyethylene, high- or low-density polypropylene and any combination thereof.

24. The device of claim 10, further comprising at least one plunger enclosed within said at least one chamber, said at least one plunger comprising at least one sealing member adapted to seal said at least one chamber and to prevent flow of said pressurized fluid; further wherein linear movement of said at least one plunger moves said at least one sealing member and creates a gap through which said pressurized fluid exits said at least one chamber.

25. The device of claim 24, wherein said at least one sealing member is at least one o-ring adapted to seal said at least one chamber.

26. The device of claim 10, wherein said device is configured to deliver said $V_{sub}$ of said one or more substances and $V_{PF}$ pressurized fluid through said at least one fluid discharging outlet port of diameter D [mm] wherein at least one of the following is held true:
 a) $V_{PF}$ is in a range of 1 to 50 ml;
 b) $V_{sub}$ is in a range of about 0.01 to about 7 ml;
 c) $D_{in}$ and/or $D_{out}$ is in a range of 0.2 to 6 mm;
 d) $P_{PF}$ is in a range of up to about 10 barg;
 e) a pressure rate, dP/dT, of the pressurized fluid increases;
 f) a pressure velocity of the pressurized fluid is greater than 0.001 barg/ms;
 g) said pressure velocity is greater than 0.01 barg/ms;
 h) a volume rate $dV_{sub}/dT$ or $dV_{sub}/dT_{release}$ is greater than 0.0001 ml/ms;
 i) said volume rate $dV_{sub}/dT$ or $dV_{sub}/dT_{release}$ is greater than 0.001 ml/ms;
 j) said volume rate $dV_{PF}/dT$ or $dV_{PF}/dT_{release}$ is greater than 0.001 ml/ms;
 k) said volume rate $dV_{PF}/dT$ or $dV_{PF}/dT_{release}$ is greater than 0.01 ml/ms;
 l) said predetermined period of time, dT decreases; and
 m) any combination thereof.

27. The device of claim 10, wherein at least one of the following is true:
 a) said at least one body cavity is selected from a group consisting of a nasal cavity, the mouth, the throat, an ear, the vagina, the rectum, the urethra, and any combination thereof;
 b) a pressurized gas is selected from a group consisting of air, nitrogen, oxygen, carbon dioxide, helium, neon, xenon and any combination thereof;
 c) during dispensing of said one or more substances, a mixture of said predetermined volume $V_{gas}$ [ml] of said pressurized gas with said predetermined volume $V_{sub}$ [ml or mg] of said one or more substances entrained within it forms a plume of aerosol; said aerosol having a predetermined distribution, said distribution being either homogeneous or heterogeneous, said heterogeneous distribution is selected from a group consisting of: an arbitrary distribution, a distribution in which the density of said one or more substances within said mixture follows a predetermined pattern, and any combination thereof; characteristics of said aerosol selected from a group consisting of: particle size, particle shape, particle distribution, and any combination thereof, are determinable from characteristics of said device selected from a group consisting of: said predetermined volume of said pressurized gas, said predetermined volume of said one or more substances, predetermined pressure of said pressurized gas, said predetermined orifice size, and any combination thereof;
 d) said one or more substances is selected from a group consisting of a gas, a liquid, a powder, an aerosol, a slurry, a gel, a suspension and any combination thereof;
 e) said one or more substances is stored under either an inert atmosphere or under vacuum to prevent reactions during storage;
 f) a dose-response curve is substantially linear for brain concentration of said one or more substances when administered nasally via said device; and
 g) a dose-response curve for brain concentration having a fit selected from a group consisting of logarithmic, parabolic, exponential, sigmoid, power-low, and any combination thereof; of said one or more substances when administered nasally via said device.

28. The device of claim 10, wherein said pressurized fluid entrains said one or more substances in a pulsed manner, such that a plurality of portions $V_{PF}$ are configured to erupt via said at least one fluid discharging outlet port to within said at least one body cavity.

29. The device of claim 10, further comprising a safety latch, adapted to prevent accidental operation of said device.

30. The device of claim 10, wherein said one or more substances is selected from a group consisting of proteins; stem-cells; cells, organs, portions, extracts, and isolations thereof; macromolecules; RNA or other genes and proteins-encoding materials; neurotransmitters; receptor antagonists; hormones; Ketamine; Glucagon; substrates to treat one of eth followings: anaphylaxis, Parkinson, seizures and opioid overdose; epinephrine; atropine; metoclopramide; commercially available Naloxone; Esketamine; edaravone; edaravone; deutetrabenazine; ocrelizumab; safinamide; nusinersen; daclizumab; pimavanserin; aripiprazole lauroxil; cariprazine; brexpiprazole; eslicarbazepine acetate; flutemetamol F18 injection; vortioxetine; dimethyl fumarate; gadoterate meglumine; Antibody mediated brain targeting drug delivery including aducanumab, gantenerumab, bapineuzumab, solanezumab, ofatumumab CD20, BIIB033, LCN2, HMGB1; insulin; oxytocin; orexin-A; leptin; benzodiazepine i.e. midazolam; naloxone; perilly alcohol; camptothecin; phytochemicals including curcumin and chrysin; nucleotides; olanzapine; risperidone; Venlafaxin; GDF-5; zonisamide; ropinirole; plant-originated and synthetically-produced terpenes and cannabinoids, including THC and CBD; valproric acid; rivastigmine; estradiol; topiramate or an equivalent preparation comprising CAS No. 97240-79-4; MFSD2 or MFSD2A or sodium-dependent lysophosphatidylcholine symporter; and any esters, salts, derivatives, mixtures, combinations thereof, with or without a carrier, liposomes, lyophilic or water-miscible solvents, surfactants, cells, cells fractions, at a therapeutically effective concentration.

31. A method for delivering either one or more substances within at least one body cavity using a device, characterized by steps of
   a) providing at least one pierceable vial with $V_{sub}$ [ml or mg] of said one or more substances; said at least one vial having at least one fluid inlet port of diameter $D_{in}$ [mm] and at least one fluid discharging outlet port of diameter $D_{out}$ [mm], configured for placement in proximity to said at least one body cavity;
   b) configuring said at least one fluid inlet port by means of size and shape to interface a puncturing member, so that upon coupling to said at least one fluid inlet port, piercing of the at least one fluid inlet port, thereby providing said one or more substances in a fluid communication with at least one chamber configured to accept pressurized fluid at volume $V_{PF}$ [ml] and pressure $P_{PF}$ [barg]; and
   c) facilitating the flow of said pressurized fluid from said at least one chamber, via said at least one fluid inlet port, entrains said one or more substances, erupts via said at least one fluid discharging outlet port into said at least one body cavity, such that a release time of said $V_{sub}$ [ml or mg] of said one or more substances and said $V_{PF}$ [ml] of said pressurized fluid, $dT_{release}$ is less than 500 milliseconds; wherein
   i) $V_{PF}$ is in a range of 1 to 50 ml;
   ii) $V_{sub}$ is in a range of about 0.01 to about 7 ml;
   iii) $P_{PF}$ is in a range of up to about 10 barg;
   further wherein at least one of the following is being held true
   iv) $D_{in}$ or $D_{out}$ are in a range of 0.2 to 6 mm;
   v) a pressure velocity is greater than 0.001 barg/ms;
   vi) said pressure velocity is greater than 0.01 barg/ms;
   vii) a volume rate or $dV_{sub}/dT_{release}$ is greater than 0.0001 ml/ms;
   viii) said volume rate $dV_{sub}/dT_{release}$ is greater than 0.001 ml/ms;
   ix) a volume rate $dV_{PF}/dT_{release}$ is greater than 0.001 ml/ms;
   x) said volume rate $dV_{PF}/dT_{release}$ is greater than 0.01 ml/ms; and
   xi) any combination thereof;
   further wherein said step of providing said at least one vial additionally comprising step of selecting said at least one vial from a group consisting of a pierceable container, a blow-fill-seal and a form-fill-seal;
   wherein said device further comprises at least one plunger enclosed within said at least one chamber, said at least one plunger comprising at least one sealing member adapted to seal said at least one chamber and to prevent flow of said pressurized fluid; and
   wherein linear movement of said at least one plunger moves said at least one sealing member and creates a gap through which said pressurized fluid exits said at least one chamber.

32. The method of claim 31, additionally comprising at least one of the following steps:
   d) selecting said at least one body cavity from a group consisting of a nasal cavity, the mouth, the throat, an ear, the vagina, the rectum, the urethra, and any combination thereof;
   e) selecting a pressurized gas from a group consisting of: air, nitrogen, oxygen, carbon dioxide, helium, neon, xenon and any combination thereof;
   f) dispensing said one or more substances, and during said step of dispensing, forming a plume of aerosol with predetermined distribution from a mixture of a predetermined volume $V_{gas}$ [ml] of said pressurized gas and a predetermined volume $V_{sub}$ [ml or mg] entrained within it; selecting said predetermined distribution from a group consisting of: a homogeneous distribution, a heterogeneous distribution; selecting said heterogeneous distribution from a group consisting of: an arbitrary distribution, a distribution in which the density of said one or more substances within said mixture follows a predetermined pattern, and any combination thereof; selecting characteristics of said aerosol from a group consisting of: particle size, particle shape, particle distribution, and any combination thereof, are determinable from characteristics of said device selected from a group consisting of: said predetermined volume of said pressurized gas, said predetermined volume of said one or more substances, said predetermined pressure of said pressurized gas, said predetermined orifice size, and any combination thereof;
   g) selecting said one or more substances from a group consisting of: a gas, a liquid, a powder, a slurry, a gel, a suspension, and any combination thereof;
   h) storing at least one said one or more substances under either an inert atmosphere or under vacuum, thereby preventing reactions during storage; and
   i) characterizing a dose-response curve for brain concentration of said one or more substances to be of substantially linear form; and
   j) a dose-response curve for brain concentration having a fit selected from a group consisting of logarithmic, parabolic, exponential, sigmoid, power-low, and any combination thereof; of said one or more substances when administered nasally via said device.

33. The method of claim 31, wherein said one or more substances is selected from a group consisting of proteins; stem-cells; cells, organs, portions, extracts, and isolations thereof; macromolecules; RNA or other genes and proteins-encoding materials; neurotransmitters; receptor antagonists; hormones; Ketamine; Glucagon; substrates to treat one of eth followings: anaphylaxis, Parkinson, seizures and opioid overdose; epinephrine; atropine; metoclopramide; commercially available Naloxone; Esketamine; edaravone; valbenazine; deutetrabenazine; ocrelizumab; safinamide; nusinersen; daclizumab; pimavanserin; aripiprazole lauroxil; cariprazine; brexpiprazole; eslicarbazepine acetate; flutemetamol F18 injection; vortioxetine; dimethyl fumarate; gadoterate meglumine; Antibody mediated brain targeting drug delivery including aducanumab, gantenerumab, bapineuzumab, solanezumab, ofatumumab CD20, BIIB033, LCN2, HMGBI; insulin; oxytocin; orexin-A; leptin; benzodiazepine i.e. midazolam; naloxone; perillyl alcohol; camptothecin; phytochemicals including curcumin and chrysin; nucleotides; olanzapine; risperidone; Venlafaxin; GDF-5; zonisamide; ropinirole; plant-originated and synthetically-produced terpenes and cannabinoids, including THC and CBD; valproric acid; rivastigmine; estradiol; topiramate or an equivalent preparation comprising CAS No. 97240-79-4; MFSD2 or MFSD2A or sodium-dependent lysophosphatidylcholine symporter; and any esters, salts, derivatives, mixtures, combinations thereof, with or without a carrier, liposomes, lyophilic or water-miscible solvents, surfactants, cells, cells fractions, at a therapeutically effective concentration.

34. The method of claim 31, wherein said puncturing member is adapted to pierce said at least one vial by means of a screw mechanism, such that rotation of a nosepiece cover along said screw mechanism in a base enables said pierce of said at least one fluid inlet port in in said at least one vial by means of said puncturing member.

35. The method of claim 31, wherein said at least one sealing member is at least one o-ring adapted to seal said at least one chamber.

36. The method of claim 31, wherein said at least one chamber is a container adapted to hold said pressurized fluid at said $P_{PF}$ for prolong periods of time.

37. The method of claim 31, wherein said at least one vial is made of at least one material selected from a group consisting of high- or low-density polyethylene, high- or low-density polypropylene and any combination thereof.

38. A method for delivering either one or more substances within at least one body cavity, characterized by steps of:
   a) providing a device comprising:
      i) at least one pierceable vial comprising $V_{sub}$ [ml or mg] of said one or more substances; said at least one vial having at least one fluid inlet port of diameter $D_{in}$ [mm] and at least one fluid discharging outlet port of diameter $D_{out}$ [mm], configured for placement in proximity to said at least one body cavity; and
      ii) a nosepiece cover configured by means of size and shape to cover at least partially a nosepiece of the device;
   b) providing the device comprising:
      i) at least one chamber configured to confine pressurized fluid at volume $V_{PF}$ [ml] and pressure $P_{PF}$ [barg]; and
      ii) at least one puncturing member; said at least one fluid inlet port of said at least one vial configured by means of size and shape to interface with said at least one puncturing member;
   c) actuating said device by piercing said at least one vial in said at least one fluid inlet port, by means of said at least one puncturing member; and
   d) releasing said volume $V_{PF}$ [ml] of said pressurized fluid at pressure $P_{PF}$ [barg] within a short period of time, <500 milliseconds (dT); out of said at least one chamber, via said at least one fluid inlet thereby entraining said one or more substances and erupting via said at least one fluid discharging outlet port into said at least one body cavity, such that a release time of said $V_{sub}$ [ml or mg] of said one or more substances and said $V_{PF}$ [ml] of said pressurized fluid, $dT_{release}$ is less than 500 milliseconds.

39. The method of claim 38, wherein said nosepiece cover and said nosepiece are coupled to each other.

40. The method of claim 39, wherein said coupling between said nosepiece cover and said nosepiece is reversible.

41. The method of claim 38, wherein removal of said nosepiece cover results in piercing said at least one vial to provide said at least one fluid discharging outlet port.

42. The method of claim 38, wherein removal of said nosepiece cover is obtained by at least one action selected from a group consisting of sliding said nosepiece cover along said device, rotating said nosepiece cover around said device, rotating said nosepiece cover around a hinge on the exterior of said device and any combination thereof.

43. The method of claim 38, wherein said nosepiece cover comprises at least one nosepiece puncturing member adapted to pierce said at least one vial to enable said at least one fluid discharging outlet port.

44. The method of claim 38, wherein said nosepiece comprises at least one port through which said one or more substances exits said device, such that said nosepiece cover seals said at least one port and removal thereof removes said seal.

45. The method of claim 38, wherein said at least one vial is selected from a group consisting of pierceable container, a blow-fill-seal and a form-fill-seal.

46. The method of claim 38, wherein said actuation is performed by means of rotation of said nosepiece cover over a base.

47. The method of claim 46, wherein said rotation is of at least 10 degrees.

48. The method of claim 46, wherein said at least one puncturing member is adapted to pierce said at least one vial by means of a screw mechanism, such that rotation of said nosepiece cover along said screw mechanism in said base enables said pierce of said at least one fluid outlet discharging port in said at least one vial by means of said at least one puncturing member.

49. The method of claim 38, wherein said at least one chamber is a container adapted to hold said pressured fluid at said $P_{PF}$ for prolong periods of time.

50. The method of claim 38, additionally comprising an activation mechanism adapted to enable the release of said pressurized fluid out of said at least one chamber.

51. The method of claim 50, wherein said at least one vial is made of at least one material selected from a group consisting of high- or low-density polyethylene, high- or low-density polypropylene and any combination thereof.

52. The method of claim 38, wherein said device additionally comprises at least one plunger enclosed within said at least one chamber, said at least one plunger comprising at least one sealing member adapted to seal said at least one chamber and to prevent flow of said pressurized fluid; further wherein linear movement of said at least one plunger moves said at least one sealing member and creates a gap through which said pressurized fluid exit said at least one chamber.

53. The method of claim 52, wherein said at least one sealing member is at least one o-ring adapted to seal said chamber.

54. The method of claim 38, wherein said device is configured to deliver said $V_{sub}$ of said one or more substances and $V_{PF}$ of said pressurized fluid through said at least one fluid discharging outlet port of diameter D [mm] wherein at least one of the following is held true:
   e) $V_{PF}$ is in a range of 1 to 50 ml;
   f) $V_{sub}$ is in a range of about 0.01 to about 7 ml;
   g) $D_{in}$ and/or $D_{out}$ is in a range of 0.2 to 6 mm;
   h) $P_{PF}$ is in a range of about 0 to about 10 barg;
   i) a pressure rate, dP/dT increases;
   j) a pressure velocity is greater than 0.001 barg/ms;
   j) said pressure velocity is greater than 0.01 barg/ms;
   l) a volume rate $dV_{sub}/dT$ or $dV_{sub}/dT_{release}$ is greater than 0.0001 ml/ms;
   m) said volume rate $dV_{sub}/dT$ or $dV_{sub}/dT_{release}$ is greater than 0.001 ml/ms;
   n) a volume rate $dV_{PF}/dT$ or $dV_{PF}/dT_{release}$ is greater than 0.001 ml/ms;
   o) said volume rate $dV_{PF}/dT$ or $dV_{PF}/dT_{release}$ is greater than 0.01 ml/ms; and
   p) any combination thereof.

55. The method of claim 38, additionally comprising at least one of the following steps:
   e) selecting said at least one body cavity from a group consisting of a nasal cavity, the mouth, the throat, an ear, the vagina, the rectum, the urethra, and any combination thereof;

f) selecting a pressurized gas from a group consisting of: air, nitrogen, oxygen, carbon dioxide, helium, neon, xenon and any combination thereof;

g) dispensing said one or more substances, and during said step of dispensing, forming a plume of aerosol with predetermined distribution from a mixture of said predetermined volume $V_{gas}$ [ml] of said pressurized gas and said predetermined volume $V_{sub}$ [ml or mg] entrained within it; selecting said predetermined distribution from a group consisting of: a homogeneous distribution, a heterogeneous distribution; selecting said heterogeneous distribution from a group consisting of: an arbitrary distribution, a distribution in which the density of said one or more substances within said mixture follows a predetermined pattern, and any combination thereof; selecting characteristics of said aerosol from a group consisting of: particle size, particle shape, particle distribution, and any combination thereof, are determinable from characteristics of said device selected from a group consisting of: said predetermined volume of said pressurized gas, said predetermined volume of said one or more substances, said predetermined pressure of said pressurized gas, said predetermined orifice size, and any combination thereof;

h) selecting said one or more substances from a group consisting of: a gas, a liquid, a powder, a slurry, a gel, a suspension, and any combination thereof;

i) storing at least one said one or more substances under either an inert atmosphere or under vacuum, thereby preventing reactions during storage; and j) characterizing a dose-response curve for brain concentration of said one or more substances to be of substantially linear form; and k) a dose-response curve for brain concentration having a fit selected from a group consisting of logarithmic, parabolic, exponential, sigmoid, power-low, and any combination thereof; of said one or more substances when administered nasally via said device.

56. The method of claim 38, wherein said one or more substances is selected from a group consisting of proteins; stem-cells; cells, organs, portions, extracts, and isolations thereof; macromolecules; RNA or other genes and proteins-encoding materials; neurotransmitters; receptor antagonists; hormones; Ketamine; Glucagon; substrates to treat one of eth followings: anaphylaxis, Parkinson, seizures and opioid overdose; epinephrine; atropine; metoclopramide; commercially available Naloxone or Narcan products; Esketamine; edaravone; valbenazine; deutetrabenazine; ocrelizumab; safinamide; nusinersen; daclizumab; pimavanserin; aripiprazole lauroxil; cariprazine; brexpiprazole; eslicarbazepine acetate; flutemetamol F18 injection; vortioxetine; dimethyl fumarate; gadoterate meglumine; Antibody mediated brain targeting drug delivery including aducanumab, gantenerumab, bapineuzumab, solanezumab, ofatumumab CD20, BIIB033, LCN2, HMGBI; insulin; oxytocin; orexin-A; leptin; benzodiazepine i.e. midazolam; naloxone; perillyl alcohol; camptothecin; phytochemicals including curcumin and chrysin; nucleotides; olanzapine; risperidone; Venlafaxin; GDF-5; zonisamide; ropinirole; plant-originated and synthetically-produced terpenes and cannabinoids, including THC and CBD; valproric acid; rivastigmine; estradiol; topiramate or an equivalent preparation comprising CAS No. 97240-79-4; MFSD2 or MFSD2A or sodium-dependent lysophosphatidylcholine symporter; and any esters, salts, derivatives, mixtures, combinations thereof, with or without a carrier, liposomes, lyophilic or water-miscible solvents, surfactants, cells, cells fractions, at a therapeutically effective concentration.

* * * * *